(12) United States Patent
Inoue

(10) Patent No.: US 8,267,683 B2
(45) Date of Patent: Sep. 18, 2012

(54) APPARATUS FOR FORMING LAYERED OBJECT

(75) Inventor: Tomoyuki Inoue, Kyoto (JP)

(73) Assignee: Shofu Inc., Kyoto (JP)

( * ) Notice: Subject to any disclaimer, the term of this patent is extended or adjusted under 35 U.S.C. 154(b) by 1312 days.

(21) Appl. No.: 11/922,291

(22) PCT Filed: Jun. 21, 2006

(86) PCT No.: PCT/JP2006/312387
§ 371 (c)(1),
(2), (4) Date: Dec. 14, 2007

(87) PCT Pub. No.: WO2007/013240
PCT Pub. Date: Feb. 1, 2007

(65) Prior Publication Data
US 2009/0025638 A1    Jan. 29, 2009

(30) Foreign Application Priority Data

Jul. 27, 2005    (JP) ................................. 2005-217991

(51) Int. Cl.
B29C 47/00    (2006.01)
B05B 7/00    (2006.01)
A01J 21/00    (2006.01)

(52) U.S. Cl. ........ 425/145; 118/308; 425/215; 425/375; 425/456

(58) Field of Classification Search .................... 425/199
See application file for complete search history.

(56) References Cited

U.S. PATENT DOCUMENTS

| | | | | |
|---|---|---|---|---|
| 3,282,207 A * | 11/1966 | Plymale | ........................ | 101/114 |
| 4,124,411 A * | 11/1978 | Meuleman et al. | ............. | 136/258 |
| 5,474,719 A * | 12/1995 | Fan et al. | ....................... | 264/401 |
| 5,753,274 A * | 5/1998 | Wilkening et al. | .......... | 425/174.4 |
| 5,838,413 A * | 11/1998 | Matoba et al. | ................. | 349/155 |
| 6,405,095 B1 * | 6/2002 | Jang et al. | ...................... | 700/118 |
| 7,389,154 B2 * | 6/2008 | Hunter et al. | .................. | 700/119 |
| 2002/0041818 A1 * | 4/2002 | Abe et al. | ........................... | 419/7 |
| 2005/0029711 A1 * | 2/2005 | Abe et al. | ....................... | 264/497 |
| 2005/0208168 A1 * | 9/2005 | Hickerson et al. | .......... | 425/174.4 |

FOREIGN PATENT DOCUMENTS

| | | |
|---|---|---|
| JP | 2003-276093 | 9/2003 |
| JP | 2004-344623 | 12/2004 |
| JP | 2004344623 A * | 12/2004 |
| JP | 2005-059477 | 3/2005 |
| WO | 03/016030 | 2/2003 |

* cited by examiner

Primary Examiner — Dah-Wei Yuan
Assistant Examiner — Charles Capozzi
(74) Attorney, Agent, or Firm — Hamre, Schumann, Mueller & Larson, P.C.

(57) ABSTRACT

A layered-object forming apparatus (1) includes a holding mechanism (10) that holds a base (12), a liquid applying device (20) that applies a liquid to a predetermined position from above the base, a powder applying device (30) that allows a powder to fall from above the base, and a powder removing device that removes an unconsolidated powder on the base. Then, a process of applying the liquid by the liquid applying device, subsequently applying the powder by the powder applying device, subsequently consolidating the liquid and the powder applied onto the liquid and then removing the powder that has not been consolidated with the liquid by the powder removing device is repeated, thereby forming a three-dimensional structure on the base. Thus, it is possible to produce a three-dimensional structure that at least partially has a smooth surface, thus allowing omission or simplification of a surface smoothing treatment.

17 Claims, 26 Drawing Sheets

APPARATUS FOR FORMING LAYERED OBJECT

TECHNICAL FIELD

The present invention relates to a layered-object forming apparatus for layering consolidated portions that are each formed by consolidation of a liquid and powder so as to produce a desired three-dimensional structure.

BACKGROUND ART

In the dental clinical field and dental research, the dental structural materials such as orthodontic brackets, orthodontic instruments, inlays, onlays, bridges, core materials, implant upper structures, partial dentures, complete dentures, various casts, experimental jigs and experimental structural materials are manufactured by a complex method including many steps, which mainly combine manual mold making, production of replicated model, waxing-up, investing, dewaxing, mold, kneading, polishing, etc. In order to carry out this method, the correct knowledge for procuring a wide variety of materials and instruments and using and applying them in their suitable ways is essential. Further, adequate learning and skill are required for the operation. Accordingly, it is very laborious and time-consuming to manufacture the dental structural materials, so that there is a limit to the improvement of manufacturing efficiency and productivity. Also, since errors are inevitable due to several repetitions of mold making and casting processes, final products sometimes have unsatisfactory adaptability and color tones. In order to solve these problems, adjusting and modifying operations that need further skill, trouble and time have to be undertaken.

To address this issue, based on a computer processing technology that has advanced considerably in recent years, a large number of methods for improving the quality and production efficiency have been developed.

JP 2004-344623 A and JP 2005-59477 A describe layered-object forming apparatuses for forming powder into layers on a forming table so as to produce a desired three-dimensional structure. The following is a brief description thereof.

FIG. 26 is a perspective view showing a schematic configuration of a conventional layered-object forming apparatus 100. As shown in this figure, horizontal axes that are perpendicular to each other are indicated by an X axis and a Y axis, and a vertical axis is indicated by a Z axis. In FIG. 26, numeral 110 denotes a forming table that can be lifted and lowered in the Z-axis direction, numeral 120 denotes a container including a wall surrounding the horizontal periphery of the forming table 110, numeral 130 denotes a powder feeder that disperses powder on the forming table 110, numeral 140 denotes a liquid feeder that delivers a liquid on the forming table 110, numeral 150 denotes a leveling member that levels off an upper surface of the powder dispersed on the forming table 110, and numeral 160 denotes a light source that emits a light beam for photopolymerization of the delivered liquid. For easier understanding of the structure, in FIG. 26, the container 120 is indicated by chain double-dashed lines so that the forming table 110 therein is seen through it.

The powder feeder 130 has a powder dispersion width that is substantially the same as the dimension of the forming table 110 in the Y-axis direction. The powder feeder 130 moves in the X-axis direction while dispersing the powder, so that the powder is dispersed on an overall surface of the forming table 110.

The leveling member 150 has a lower end, which is provided with a leveling edge 151 extending in the Y-axis direction. The leveling member 150 moves in the X-axis direction while allowing the leveling edge 151 to slide on an upper surface 122 of the container 120.

The liquid feeder 140 is moved in the Y-axis direction by a uniaxial guiding mechanism 148. This uniaxial guiding mechanism 148 is driven in the X-axis direction by a driving mechanism, which is not shown in the figure. In other words, the liquid feeder 140 delivers the liquid toward the forming table 110 at desired positions while scanning along the X-axis and Y-axis directions over the forming table 110.

The forming table 110 is lowered at a constant pitch by a driving mechanism, which is not shown in the figure. The powder is formed as layers on the forming table 110, with the thickness of one layer corresponding to this single pitch.

The method for producing a three-dimensional structure will be described in detail with reference to FIGS. 27A to 27E.

FIG. 27A shows the state in which a plurality of layers (two layers in the figure) of the powder already are formed on the forming table 110. Numeral 171 denotes an uppermost layer in the plurality of powder layers deposited on the forming table 110, numeral 172 denotes a consolidated portion in the uppermost layer 171 formed by polymerizing the liquid, numeral 173 denotes a powder layer deposited immediately before the uppermost layer 171, and numeral 174 denotes a consolidated portion in the powder layer 173 formed by polymerizing the liquid.

In this state, as shown in FIG. 27A, while the powder feeder 130 is being moved in the X-axis direction, powder 134 is dispersed on the forming table 110 from a slit 132 of the powder feeder 130.

Next, as shown in FIG. 27B, the leveling member 150 is moved in the X-axis direction, thereby conforming an upper surface of the powder 134 so as to have the same height as the upper surface 122 of the container 120. In this manner, a powder layer 175 having a uniform thickness is formed on the uppermost layer 171.

Subsequently, as shown in FIG. 27C, while the liquid feeder 140 is being moved, the liquid is delivered toward the powder layer 175 at a desired position. Numeral 176 indicates a portion in the powder layer 175 to which the liquid is applied.

Thereafter, as shown in FIG. 27D, light is irradiated using the light source 160, thereby polymerizing and solidifying the liquid applied to the powder layer 175. When the liquid is solidified, the powder in a region to which the liquid has been applied is integrated. In this way, a consolidated portion 177 is formed in the powder layer 175.

Then, the forming table 110 is lowered by a predetermined pitch, and the processes of FIGS. 27A to 27D described above are carried out. The above-mentioned processes are repeated necessary times.

Finally, unconsolidated powder on the forming table 110 is removed, thus obtaining a three-dimensional structure 170 in which the consolidated portions 174, 172 and 177, etc. are integrated as shown in FIG. 27E.

By utilizing this method, it also is possible to produce three-dimensional structures with a complex shape, for example, dental structural materials.

DISCLOSURE OF INVENTION

Problem to be Solved by the Invention

In general, the surface of dental structural materials has to be smooth. Especially in partial dentures and complete dentures, the smoothness of the surface that contacts a mucosal surface in a patient's mouth is extremely important because it greatly affects the wearing comfort of the dentures.

However, in the conventional layered-object forming apparatus described above, steps due to layering and minute irregularities due to powder remain on the surface of the three-dimensional structure immediately after completion. Thus, in particular, it has been necessary to subject the surface that contacts the mucosal surface in the mouth to post treatments such as application of a surface lubricant and polishing.

It is an object of the present invention to provide a layered-object forming apparatus capable of producing a three-dimensional structure that at least partially has a smooth surface, thus allowing omission or simplification of a surface smoothing treatment.

Means for Solving Problem

A layered-object forming apparatus according to the present invention includes a holding mechanism that holds a base, a liquid applying device that applies a liquid to a predetermined position from above the base, a powder applying device that allows a powder to fall from above the base, and a powder removing device that removes an unconsolidated powder on the base. A process of applying the liquid by the liquid applying device, subsequently applying the powder by the powder applying device, subsequently consolidating the liquid and the powder applied onto the liquid and then removing the powder that has not been consolidated with the liquid by the powder removing device is repeated, thereby forming a three-dimensional structure on the base.

EFFECTS OF THE INVENTION

In accordance with the present invention, since the liquid is applied first to the base, the surface of the three-dimensional structure that has contacted the base truly reflects the surface shape of the base, so that the steps due to layering and minute irregularities due to powder can be reduced. Therefore, it is possible to achieve a three-dimensional structure with a smooth surface. As a result, the surface smoothing treatment can be omitted or simplified.

For example, in the case where a partial denture or a complete denture is produced, since the adaptability to the mucosal surface in the mouth improves considerably, the adjustment work at the time when a patient puts the denture in his/her mouth can be reduced greatly. Thus, it is possible to reduce the burden on the patient and the labor and working time of a dentist.

Also, a large number of processes that have been performed conventionally by a dental technician when producing a denture can be simplified greatly.

Furthermore, since the adaptability of the denture to the mucosal surface improves, it becomes possible to reduce the frequency at which the denture must be remade because of its poor adaptability.

Also, since the adaptability of the denture to the mucosal surface improves and the variation in adaptability according to different workers decreases, it becomes less necessary for a patient to use a denture stabilizer. Consequently, the occlusal vertical dimension is consistent with that at the time of designing the denture, so that an occlusal interference or an anomaly of a temporomandibular joint, which is caused by variations in the occlusal vertical dimension due to the use of the denture stabilizer, can be made less likely to occur.

Moreover, since it is possible to reduce the period from the time when a denture becomes necessary until a patient actually puts on the denture, the time during which the patient feels inconvenience until the completion of the denture can be shortened.

Further, if the denture breaks, a highly-precise denture can be reproduced easily. Therefore, it is possible to shorten extremely the time required for the diagnosis for reproduction and the waiting time until completion.

DESCRIPTION OF THE INVENTION

Figure 1:
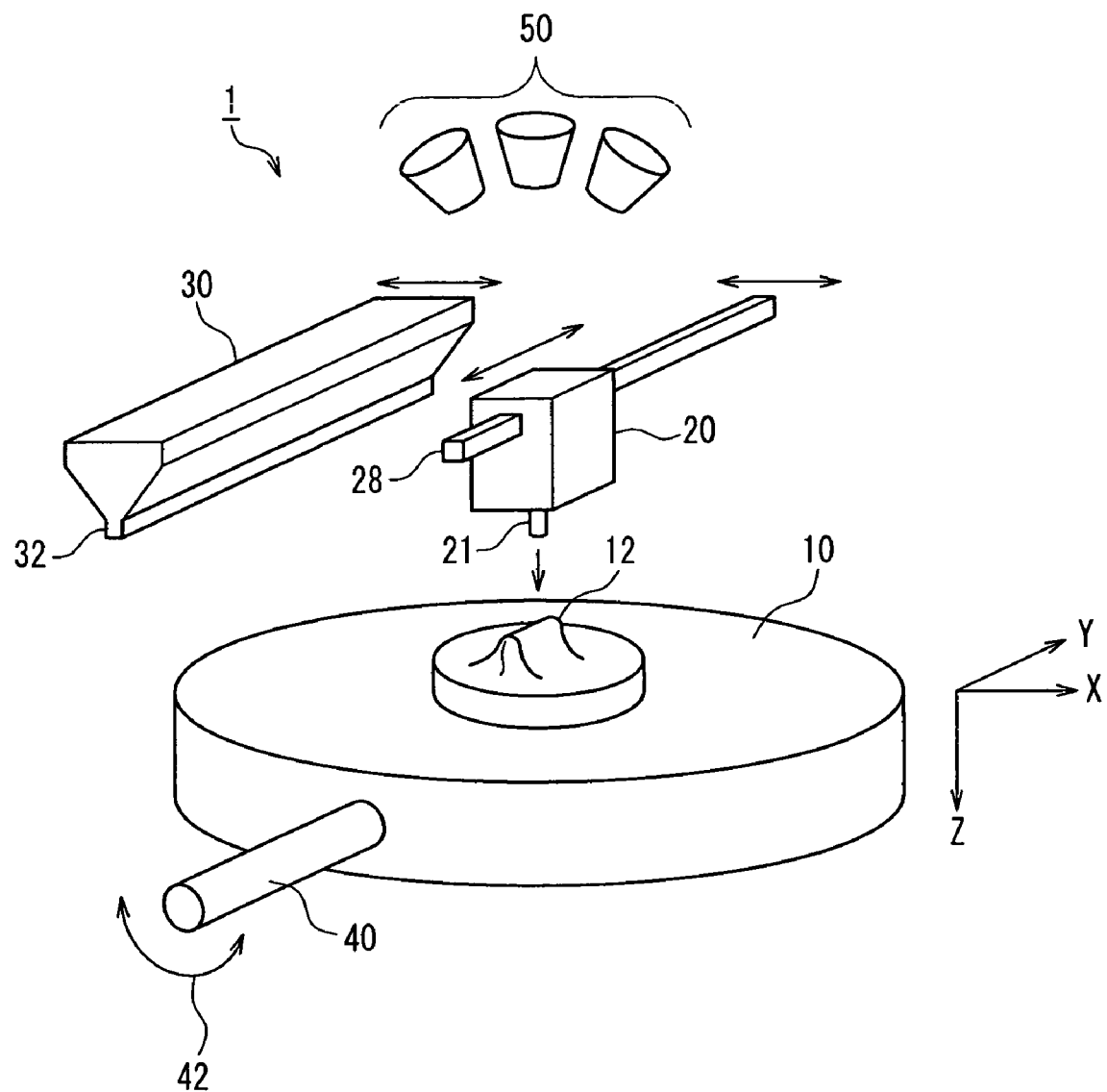
FIG. 1 is a perspective view showing a schematic configuration of a layered-object forming apparatus according to Embodiment 1 of the present invention.

It is preferable that the holding mechanism is a table on which the base is placed. This makes it possible to produce a relatively large three-dimensional structure.

Alternatively, the holding mechanism may be a rod-like member that is inserted in the base. This makes it possible to produce a relatively small three-dimensional structure.

It is preferable that the powder removing device includes a rotating mechanism for rotating the base and allows the unconsolidated powder to fall by gravity and be removed. Alternatively, it is preferable that the powder removing device includes an air nozzle for ejecting a gas and blows off and removes the unconsolidated powder with the gas. Alternatively, it is preferable that the powder removing device includes a suction nozzle for sucking an atmosphere and allows the unconsolidated powder to be sucked into the suction nozzle and removed. In any case, the unconsolidated powder can be removed in a simple manner.

It is preferable that the layered-object forming apparatus according to the present invention further includes a vibration generating device that vibrates the holding mechanism. This makes it possible to remove the unconsolidated powder easily within a short time.

It is preferable that the layered-object forming apparatus according to the present invention further includes a container surrounding a horizontal periphery of the table, a leveling member that levels off the powder heaped in the container, and a lifting and lowering mechanism that varies a relative position between the container and the table along a height direction. This makes it possible to layer the consolidated portion layers that are formed by dispersing the powder so as to have a certain thickness and then applying the liquid onto the powder, thus producing a three-dimensional structure.

It is preferable that the holding mechanism is a table on which the base is placed, and the layered-object forming apparatus further includes a container surrounding a horizontal periphery of the table, a leveling member that levels off the powder heaped in the container, and a lifting and lowering mechanism that varies a relative position between the container and the table along a height direction. Further, it is preferable that a process of applying the powder into the container by the powder applying device, subsequently leveling off the powder by the leveling member, subsequently applying the liquid by the liquid applying device and then lowering the table relative to the container by the lifting and lowering mechanism is repeated, thereby forming a further three-dimensional structure on the three-dimensional structure. In this way, a three-dimensional structure with a complex shape such as an undercut shape can be produced more easily.

It is preferable that the layered-object forming apparatus according to the present invention further includes a three-dimensional measuring device that measures the base or the three-dimensional structure formed on the base. This makes it easier to measure the shape of the base, position the base with respect to the holding mechanism and measure the shape of the three-dimensional structure formed on the base.

A lower surface of the powder applying device may be provided with a plurality of screens that are stacked so as to block an opening formed on the lower surface. In this case, it is preferable that each of the plurality of screens is provided with a plurality of holes through which the powder can pass. Also, it is preferable that falling of the powder is controlled by controlling a movement of at least one of the plurality of screens relative to the other. In this way, regardless of the shape and size of the opening, the falling of powder easily can be controlled to start and stop. In other words, this improves the degree of flexibility in designing an area on which the powder falls from the powder applying device.

It is preferable that one of the plurality of screens is an endless screen obtained by connecting both ends of a belt-like screen in annular form. By moving the endless screen continuously in one direction, it is possible to allow the powder to fall stably and continuously.

The powder applying device may include an inclined substrate and a plurality of dividing plates that are arranged on the substrate. In this case, it is preferable that the plurality of dividing plates are divided into a plurality of tiers in a vertical direction. Also, it is preferable that more dividing plates are included in an N+1th tier than in an Nth tier from a top when N is a natural number. Further, it is preferable that each of the dividing plates divides a powder flow from above into two. In this way, it becomes possible to disperse a large volume of the powder in a wide area, so that the time for forming a three-dimensional structure can be reduced.

It is preferable that the layered-object forming apparatus according to the present invention further includes an inclination mechanism that varies an orientation of the base in at least two directions including a first direction and a second direction different from the first direction. In this case, it is preferable to apply the liquid and allow the powder to fall in each of a state where the base faces the first direction and a state where the base faces the second direction. In this way, even when a recess is formed on the surface of the base, for example, the consolidated portion layer can be formed in the recess. Thus, it is possible to form a three-dimensional structure with a desired shape easily regardless of the shape of the base.

In the above description, the liquid may be applied to and the powder may be allowed to fall on the base facing the first direction repeatedly so as to form on the base a first consolidated portion layer that is formed by consolidation of the liquid and the powder, and then the liquid may be applied to and the powder may be allowed to fall on the base facing the second direction repeatedly so as to form on the base a second consolidated portion layer that is formed by consolidation of the liquid and the powder.

Alternatively, a process of applying the liquid to and allowing the powder to fall on the base facing the first direction so as to form on the base a first consolidated portion layer that is formed by consolidation of the liquid and the powder, and a process of applying the liquid to and allowing the powder to fall on the base facing the second direction so as to form on the base a second consolidated portion layer that is formed by consolidation of the liquid and the powder may be repeated alternately.

In any case, it is possible to form a three-dimensional structure with a desired shape in an efficient manner.

In the following, the present invention will be described in detail by way of embodiments.

(Embodiment 1)

FIG. 1 is a perspective view showing a schematic configuration of a layered-object forming apparatus 1 according to Embodiment 1 of the present invention. As shown in this figure, horizontal axes that are perpendicular to each other are indicated by an X axis and a Y axis, and a vertical axis is indicated by a Z axis.

A base 12 is held on a forming table (a holding mechanism) 10. A three-dimensional structure is layered and formed on the base 12. One end of an arm 40 whose longitudinal direction corresponds to a Y-axis direction is coupled to the forming table 10, and the other end of the arm 40 is connected to a rotation driving mechanism, which is not shown in the figure. The rotation driving mechanism rotates the arm 40 in directions indicated by arrows 42 so as to flip the forming table 10.

A liquid feeder (a liquid applying device) 20 delivers a liquid from above the base 12 and allows the liquid to fall. The liquid feeder 20 moves in the Y-axis direction by a uniaxial guiding mechanism 28. This uniaxial guiding mechanism 28 is driven in an X-axis direction by a driving mechanism, which is not shown in the figure. In other words, the liquid feeder 20 delivers the liquid at desired positions while scanning along the X-axis direction and the Y-axis direction over the base 12.

A powder feeder (a powder applying device) 30 has a lower surface provided with a slit 32 for allowing powder to fall. The powder feeder 30 has a powder dispersion width that is at least equal to or greater than the dimension of the base 12 in the Y-axis direction. The powder feeder 30 moves in the X-axis direction while dispersing the powder, thereby allowing the powder to fall from above the base 12.

A three-dimensional measuring unit 50 is provided above the forming table 10.

In the following, a method for producing a three-dimensional structure using the above-noted layered-object forming apparatus 1 will be described.

Figure 2A:
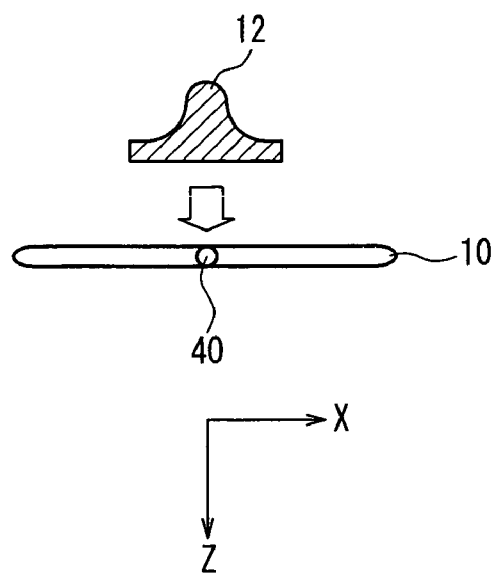
FIG. 2A is a sectional view showing a process in a method for producing a three-dimensional structure using the layered-object forming apparatus according to Embodiment 1 of the present invention.

First, as shown in FIG. 2A, the base 12 is fixed onto the forming table 10. For example, in the case of producing a denture, the base 12 is a replica of a patient's alveolar ridge. The upper surface of the base 12 has the same shape as a mucosal surface in the patient's mouth.

However, in the case where a gap is desired between a final three-dimensional structure and a wearing surface in the patient's mouth in order to secure a cement space and improve the wearing comfort, a foil or a thin layer made of a metal, a resin or the like may be attached or applied partially or entirely to the surface of the base 12 as a gap provider.

Figure 2B:
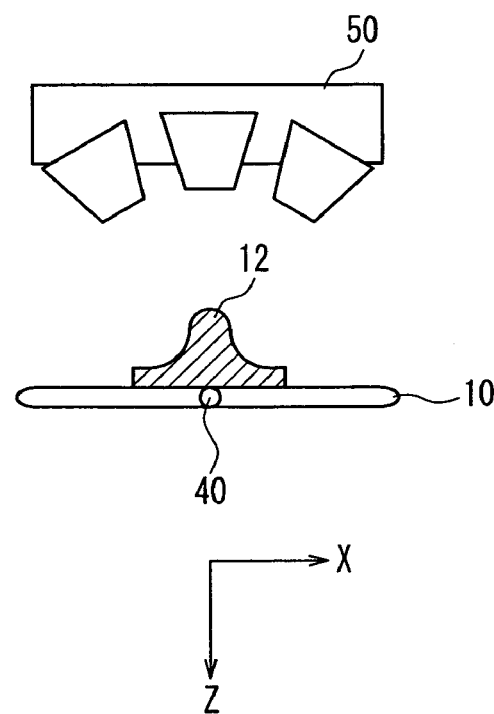
FIG. 2B is a sectional view showing a process in the method for producing a three-dimensional structure using the layered-object forming apparatus according to Embodiment 1 of the present invention.

At this time, as shown in FIG. 2B, the base 12 may be positioned accurately on the forming table 10 using the three-dimensional measuring unit 50. Also, the shape of the upper surface of the base 12 may be measured using the three-dimensional measuring unit 50.

Figure 3A:
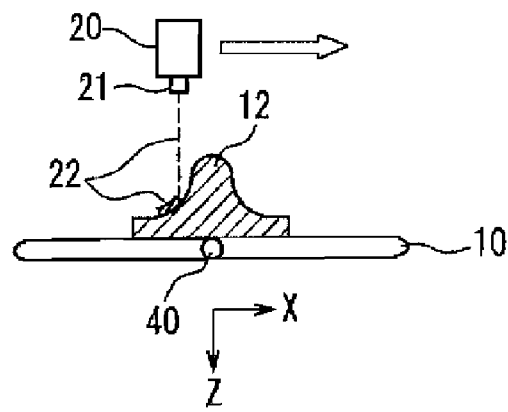
FIG. 3A is a sectional view showing a process in the method for producing a three-dimensional structure using the layered-object forming apparatus according to Embodiment 1 of the present invention.

Next, as shown in FIG. 3A, while the liquid feeder 20 is being moved, a liquid 22 is delivered from a nozzle 21 at predetermined positions. In this way, the liquid 22 adheres to the predetermined positions on the base 12.

The delivery of the liquid for forming one consolidated portion layer may be completed by a single time of scanning of the liquid feeder 20 or performed by a plurality of times of scanning. For example, in the case of using a material for swelling the powder as the liquid, the plurality of times of scanning make it possible to suppress the progress of powder swelling and to suppress blurring of the liquid and prevent the liquid from spreading beyond a desired area.

Figure 3B:
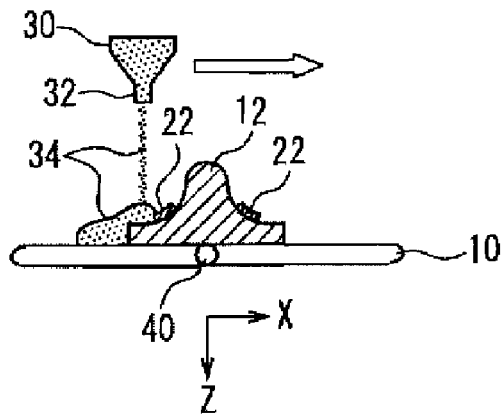
FIG. 3B is a sectional view showing a process in the method for producing a three-dimensional structure using the layered-object forming apparatus according to Embodiment 1 of the present invention.

Next, as shown in FIG. 3B, while the powder feeder 30 is being moved in the X-axis direction, powder 34 is allowed to fall from a slit 32 so that the base 12 is covered with the powder 34. In this way, in a portion to which the liquid 22 adheres, the powder is swelled by the liquid 22, and the liquid 22 is polymerized, thereby consolidating the liquid and the powder.

Figure 3C:
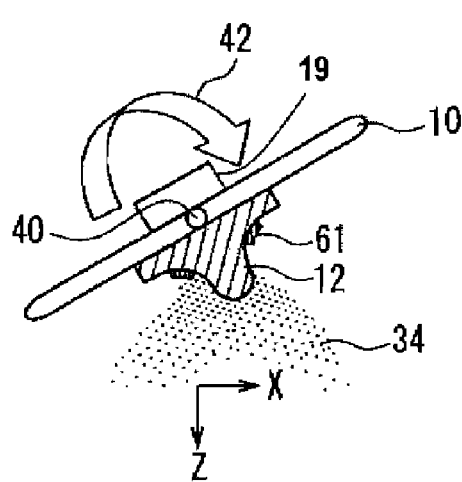
FIG. 3C is a sectional view showing a process in the method for producing a three-dimensional structure using the layered-object forming apparatus according to Embodiment 1 of the present invention.

Then, as shown in FIG. 3C, the forming table 10 is flipped via the arm 40. In this manner, surplus powder 34 on the base 12 except for the powder consolidated by the liquid 22 falls by gravity and is removed. Consequently, a consolidated portion 61 formed by consolidation of the liquid and the powder is formed on the base 12.

The forming table 10 may be provided with a vibration generating device 19 that vibrates the forming table 10. By vibrating the forming table 10 when flipping the forming table 10, it is possible to remove the surplus powder 34 easily within a short time. The vibration generating device 19 is not particularly limited and can be, for example, a device obtained by attaching an eccentric weight to a rotational shaft of an electric motor.

Figure 3D:
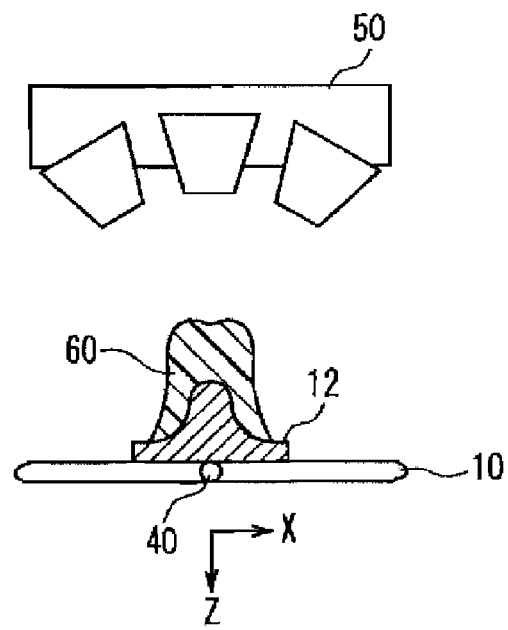
FIG. 3D is a sectional view showing a process in the method for producing a three-dimensional structure using the layered-object forming apparatus according to Embodiment 1 of the present invention.

Processes similar to FIGS. 3A to 3C are repeated necessary times, thus sequentially layering consolidated portion layers formed by consolidation of the liquid and the powder on the base 12. The position where the liquid feeder 20 applies the liquid can be varied to vary the position at which the individual consolidated portion layers are layered. As a result, as shown in FIG. 3D, a three-dimensional structure 60 made of a large number of the consolidated portion layers that are formed by the consolidation of the liquid and the powder can be formed on the base 12.

The completed shape of the three-dimensional structure 60 on the forming table 10 may be measured by the three-dimensional measuring unit 50.

Thereafter, the three-dimensional structure 60 is separated from the base 12, thus obtaining the three-dimensional structure 60 with a desired shape. If necessary, a surface finishing treatment may be carried out so as to improve a surface lubricity.

In the present invention, the liquid is applied first on the base 12. Then, the powder is dispersed, followed by consolidating the liquid and the powder. In other words, not the powder but the liquid is applied first to the surface of the base 12. Therefore, the surface of the base 12 is transferred substantially truly on the surface that has contacted the base 12 (a lower surface) of the final three-dimensional structure 60. Consequently, when the surface of the base 12 is made smooth in advance, it is possible to achieve a smooth surface similar thereto.

For example, in the case of producing a dental structural material, when the base 12 having a smooth upper surface that reproduces the shape of a mucosal surface in a patient's mouth is used, the surface to be in contact with the mucosal surface can be made smooth. Thus, it is possible to omit or simplify a surface smoothing treatment of this surface. Also, since the deterioration of a dimensional accuracy caused by the surface smoothing treatment can be reduced, the adaptability is not degraded. In this manner, it is possible to produce a dental structural material highly accurately within a short time without the work of a highly skilled worker.

In the present invention, the layer thickness (the thickness of one consolidated portion) can be varied according to the purpose of the three-dimensional structure. A smaller layer thickness increases the resolution, resulting in improvement of the dimensional accuracy and the surface smoothness.

[Powder]

The material of the powder can be one kind or a combination of plural kinds of any grains of organic substances, inorganic substances, metal oxides and the like. Although there is no particular limitation on the material of the powder, it is preferable to take the purpose of a three-dimensional structure into consideration when selecting the material. For example, in the case of producing a dental structural material, it is preferable to use a field proven material used widely in dentistry considering the safety and processability. More specifically, it is possible to use glass materials, various kinds of metal oxides, various kinds of ceramic materials, various kinds of polymers or compositions of combination of these materials. Also, a surface layer of the powder may be covered with these materials.

In the case of using resin materials, it is possible to use one kind of or a mixture of two or more kinds of methyl methacrylate polymer, ethyl methacrylate polymer and copolymer of methyl methacrylate and ethyl methacrylate, for example. In this case, the powder preferably contains at least 30 wt % (further preferably, at least 50 wt % and particularly preferably, at least 70 wt %) of powder made of the above-mentioned resin materials and further may contain one kind of or two or more kinds of organic powder, inorganic powder and metal oxide powder.

The powder also can be subjected to various kinds of surface treatment, as necessary. For example, it is possible to carry out a silane treatment and a heating treatment.

The shape of the powder is not particularly limited. It is possible to select and use suitably an amorphous shape, a spherical shape, a toroidal shape, a shape with a through hole, a clump, whisker, a rod shape, a needle shape, a porous shape, a dimpled shape or the like according to the purposes. The amorphous shape, the spherical shape, the toroidal shape and the shape with a through hole have an advantage of easy forming. The whisker, the rod shape and the needle shape are very effective in improving the strength after curing. The clump, the porous shape, the dimpled shape and the like have advantages in that they are effective in improving the adhesion between the powder and the liquid and can develop and maintain a large mechanical strength after curing.

The grain size is not particularly limited, either, but has to be smaller than one layer thickness. More specifically, it is preferable that the average grain size is 0.001 µm to 0.5 mm. The average grain size further preferably is 0.1 µm to 0.3 mm and particularly preferably is 10 µm to 0.15 mm.

The method for supplying the powder can be a method of preparing the powder in a reservoir tank and supplying the powder through a tube into the powder feeder 30, a method of providing the powder feeder 30 with a reservoir tank and allowing the powder to fall from the slit 32 by gravity, or the like. It also is possible to place a plurality of reservoir tanks and prepare plural kinds of powders with different compositions or color tones in the respective reservoir tanks, and use the plural kinds of powders or combine them in their suitable ways at the time of producing a three-dimensional structure. In the case of switching the plural kinds of powders for use, it is preferable that the supply of the powder from the reservoir tank to the slit 32 and the opening and closing of the slit 32 are controlled by a computer.

The opening width of the slit 32 in the X-axis direction preferably is at least twice, further preferably is at least 6 times as great as the maximum grain size of the powder to be used.

In order to collect efficiently the powder 34 that has been removed and fallen in the process of FIG. 3C described above, a tray, a suction device and a conveying mechanism may be provided below the forming table 10. The collected powder also can be sieved to remove dusts, and then returned to the reservoir tank for repeated use.

[Liquid]

The liquid is cured and integrated with the powder so as to serve as a binder in the consolidated portion.

As the liquid, it is possible to use a liquid that contains a polymerizable monomer as a base component and contains various kinds of additives blended according to the purposes. Also, the liquid can contain any particles, fillers, fibrous substances or the like as long as it does not impair the viscosity and various physical properties required in the practice of the present invention. Although there is no particular limitation on the material of the liquid, it is preferable that the purpose of a three-dimensional structure is considered when selecting the material. For example, in the case of producing a dental structural material, it is preferable to use a field proven material used widely in dentistry considering the safety and processability. More specifically, it is preferable to use a monomer or an oligomer that contains water, acrylic, urethane or other system as a principal component, a composition of such a monomer or an oligomer and a plasticizer, a composition of at least one kind of organic solvent, or a liquid of a mixture thereof.

The polymerizable monomer serving as the principal component in the liquid preferably is methyl methacrylate or ethyl methacrylate.

For example, it is possible to use a liquid in which 0.1 to 35 wt % of polyalkylacrylate polymer is dissolved.

When the liquid has too low a viscosity to be ejected suitably, it desirably is made to contain a component having a thickening effect. For example, polymerizable monomers with a high molecular weight such as a urethane resin and polymerizable monomers with a relatively small molecular weight that are often used as a cross-linking agent at the time of polymerization such as ethylene glycol dimethacrylate, triethylene glycol dimethacrylate, neopentyl glycol dimethacrylate and 1,6 hexanediol dimethacrylate can be used in a preferred manner.

It also is possible to prepare a plurality of liquids with different color tones and mixing (mixing the colors of) these liquids while varying the blend amount, thereby achieving a liquid with any desired color tone. Basically, a desired color tone can be obtained by a subtracting color mixture theory. The transparency is controlled by mixing a transparent liquid and an opaque liquid. In other words, an increase in the blend amount of the transparent liquid raises the transparency, whereas an increase in the blend amount of the opaque liquid lowers the transparency. When the opaque liquid is prepared using a white opaque material, it is possible to achieve improvement in lightness as well as the opacification. In order to lower the lightness, it is desired to use a black liquid.

In the case of preparing a set of color tones including two or more liquids with different color tones, the color tones to be selected are not particularly limited, and the ranges of hue, lightness and saturation are by no means limited. For example, in the case of producing a dental structural material, any color tone can be selected as long as it is consistent with the purpose of use. The number of color tones constituting the color tone set may be one, two or any number larger than two according to the intended use of the dental structural material. Although the upper limit of the number of color tones is not particularly set, it usually is preferable that the maximum number of color tones is reproduced using the least number of color tones from the viewpoint of maintaining the liquids and providing the installation space of the liquids. Accordingly, a set of 1 to 24 color tones is preferable, a set of 2 to 12 color tones is further preferable, and a set of 3 to 8 color tones is particularly preferable. In the case of the set of 3 to 8 color tones, it is preferable to include red, yellow and black without fail. By combining them with white, which is the color of the powder, it is possible to reproduce most of the color tones of teeth and gums. Further, the set of color tones can be prepared by adding colors for adjusting the lightness and saturation or colors used for characterization.

Alternatively, it also is possible to use liquids adjusted to have respective color tones of enamels, dentin and gums according to individual parts. This method is inferior to the method of mixing plural liquids having different color tones in terms of variation of color tones and fine adjustment of color tones. However, when the color tones to be reproduced are substantially limited as in the case of producing an everyday prosthetic appliance, this method is reasonable because the kinds of liquids to be prepared and the stockpiles can be minimized.

It also is possible to use a set of plural liquids that have different physical and/or chemical properties after polymerization. For example, a liquid containing a resin having an excellent toughness as a principal component is used for forming an inside of the tooth, and a liquid containing a resin having a high hardness and an excellent abrasion resistance as a principal component is used for forming an enamel part, thereby making it possible to produce a denture that is not abraded or broken easily and endures a long-term use.

Of course, it also is possible to constitute a set of liquids by combining various liquids having different color tones and different physical properties optionally. This method makes it possible to improve both aesthetic properties and functionality compared with the conventional method of producing a dental structural material by manual work or automated machine production, and thus is applicable to a wide range of uses for the dental clinical field and research.

[Liquid Feeder]

The liquid feeder 20 that delivers a certain amount of the liquid from above the base 12 is connected to a liquid reservoir tank directly or indirectly via a tube. The liquid reservoir tank may be disposed together with or separately from the liquid feeder 20. The liquid reservoir tank may be a replaceable cartridge. This makes it easier to change the kinds of the liquid and replenish the tank with the liquid.

The bore of the nozzle 21 of the liquid feeder 20 from which the liquid is delivered can be selected suitably considering the delivery amount, the resolution, the shape and size of a three-dimensional structure to be produced, etc., and preferably ranges from 1 to 500 μm. In the case of producing a dental structural material, the bore ranges preferably from 3 to 200 μm and further preferably from 6 to 50 μm.

The principle of operation of the liquid feeder 20 can vary in many ways. For example, it is possible to adopt a system of delivering the liquid by the pressure of a gas such as the air or a nitrogen gas, a system of blowing off a slight amount of the liquid using a piezoelectric element, the Bubble Jet (registered trademark) system, a system of electrically charging the liquid and delivering the liquid by utilizing electric attraction, a system of blowing off the liquid by utilizing an energy such as ultrasonic waves, or the like. Selection can be made from these systems suitably according to the kinds of the liquid, the delivery amount, the three-dimensional structure to be produced, etc. Among them, the system of delivering the liquid by the pressure of the gas such as the air, the system using a piezoelectric element, the Bubble Jet (registered trademark) system and the like are preferable.

Two or more kinds of the liquid may be supplied to one liquid feeder 20. In this case, respective liquid supplying pipes may be connected directly to the liquid feeder 20 or integrated into one supplying pipe, which then is connected to the liquid feeder 20.

The number of the liquid feeders 20 is not limited to one but may be two or more. In that case, the individual liquid feeders 20 may be supplied with different liquids, or all the liquid feeders 20 may be supplied with the same liquid.

The number of liquid delivery nozzles provided in one liquid feeder 20 is not limited to one but may be two or more. Even in the case where the liquid feeder 20 includes only one nozzle, the liquid can be applied to desired positions on the base 12 by driving the liquid feeder 20 along the X axis and the Y axis as shown in FIG. 1.

In the case where the liquid feeder 20 has plural nozzles, all the nozzles may deliver the same liquid, or the individual nozzles may deliver different liquids. As the number of the nozzles that deliver one liquid increases, the processing speed improves.

Although there is no particular limitation on the arrangement of the plural nozzles, an inline arrangement along a straight line or a curved line or a lattice point arrangement is preferable. The arrangement of the nozzles preferably is determined considering the moving direction of the liquid feeder 20.

If a plurality of the nozzles are arranged over a range wider in the Y-axis direction than the dimension of the base 12, there is a possibility that the movement of the liquid feeder 20 in the Y-axis direction may be omitted. For example, when a plurality of the nozzles are arranged over the same range in the Y-axis direction as the width of the forming table 10, only a single movement of the liquid feeder 20 in the X-axis direction is needed for the liquid to be applied at any positions on the base 12 with any size.

Alternatively, if a plurality of the nozzles are arranged as a lattice within a range corresponding to the entire area of the forming table 10, there is a possibility that the movement of the liquid feeder may be omitted at the time of applying the liquid. However, in this case, the liquid feeder needs to be retracted at the time of applying the powder.

Furthermore, it also may be possible to provide a mechanism of varying the position of the liquid feeder 20 in the Z-axis direction, or a mechanism of rotationally-driving an entire mechanism of moving the liquid feeder 20 in the X-axis direction and/or the Y-axis direction within the horizontal plane.

It also may be possible to supply different liquids to different nozzles, respectively, and control the delivery amounts of the individual nozzles independently from one another. For example, in the case of using a plurality of the liquids with different color tones, a three-dimensional structure whose color tone varies in each part can be produced by varying the delivery amount of each of the nozzles. Also, in the case of using a plurality of the liquids that are adjusted to have different physical properties after consolidation, a three-dimensional structure whose physical property varies in each part can be produced by varying the delivery amount of each of the nozzles.

[Liquid Consolidation Method]

The liquid is polymerized and thus consolidated with the powder. A method for polymerizing the liquid is not particularly limited but can be any one or a plurality of methods used widely in an industrial field such as chemical polymerization, photopolymerization, thermal polymerization, ultraviolet polymerization, near-infrared polymerization, far-infrared polymerization and ultrasonic polymerization.

In order to polymerize the liquid chemically, it is preferable to blend benzoyl peroxide in the powder and blend tertiary amine, barbituric acid or the like in the liquid, for example. In this way, when the powder is dispersed on the adhering liquid and comes into contact therewith, the powder is impregnated with the liquid and swells, and chemical polymerization catalysts that are blended respectively in the liquid and the powder contact each other so as to cause the chemical polymerization, leading to curing. In this case, the polymerization and curing occur only in the part to which the liquid is applied and do not occur in the part to which the liquid is not applied. Accordingly, it is possible to collect unwanted powder that is not consolidated because no liquid has been applied thereto and to disperse the powder onto the base 12 again.

It also may be possible to heat the powder and/or the liquid in advance and, when the powder is impregnated with the liquid, promote the chemical polymerization by the thermal energy.

The method of heating the liquid is not particularly limited and can be selected freely according to the purposes. For example, the liquid delivery nozzle 21 of the liquid feeder 20 may be provided with a heater.

Providing the nozzle with the heater is accompanied by an effect of lowering the viscosity of the liquid. This makes it possible to eject a highly-viscous liquid that is not suitable for being ejected at room temperature. Such a highly-viscous liquid that is not suitable for being ejected at room temperature can be, for example, a liquid containing a filler or polyalkylmethacrylate, a liquid in which a filler or polyalkylmethacrylate is dissolved, a liquid whose entire viscosity is raised because a liquid component of part of the liquid is a highly-viscous liquid, or the like.

In the chemical polymerization method, there is no need for a polymerization operation of light irradiation every time one layer is formed. Thus, the time for the polymerization operation during the production of a three-dimensional structure becomes unnecessary, thus making it possible to achieve labor savings and reduce the production time.

Of course, one or more polymerization methods that have been used conventionally for polymerization and curing of resin materials also can be used in combination. For example, during forming, the polymerization and curing are made to proceed by chemical polymerization, and after the forming, the entire product is heated to cause a final polymerization, thereby reducing unreacted monomers and further improving the physical properties.

In the case of polymerizing the liquid chemically, there is no need for a special device for polymerizing the liquid. When the liquid and the powder are cured by the chemical polymerization reaction, an unpolymerized layer remains within the range 500 µm (further 300 µm, and especially 200 µm) deep from a surface layer that is in contact with the air. Thereafter, when the subsequent layer is formed thereon, the above-noted unpolymerized layer on the surface of lower layers and an upper layer are polymerized and cured integrally by the chemical polymerization reaction of the upper layer.

In the case of photopolymerizing the liquid, a light irradiator is disposed such that its position and orientation are adjusted so as to irradiate the base 12 with light. If necessary, it also is possible to provide a light irradiation direction control device including a computer. The liquid is delivered from above the base 12, and then the powder is dispersed and impregnated with the liquid, followed by light irradiation to cause polymerization and curing. In this case, a photopolymerization catalyst is blended only in the liquid, whereby only the part to which the liquid is applied is polymerized and cured, and the part to which no liquid is applied is not polymerized or cured. Accordingly it is possible to collect unwanted powder that is not consolidated because no liquid has been applied thereto and to disperse the powder onto the base 12 again.

In the case of thermally polymerizing the liquid, a polymerization initiator that generates a free radical when heated, for example, benzoyl peroxide or the like, is blended only in the liquid. Then, the heated powder is dispersed. By the heat of the powder, the liquid is polymerized and cured. The part to which no liquid is applied is not polymerized or cured.

In the case of polymerizing the liquid using ultraviolet rays, near-infrared rays or far-infrared rays, a light irradiating device is disposed such that its position and orientation are adjusted so as to irradiate any position on the base 12 with a beam at a predetermined wavelength. If necessary, it also is possible to provide a light irradiation direction control device including a computer. The liquid is delivered from above the base 12, and then the powder is dispersed and impregnated with the liquid, followed by irradiation of a desired position with a thin light beam to apply polymerization energy, so that only the part irradiated with the beam is polymerized and cured.

In the case of using near-infrared rays, a polymerization initiator that generates a free radical when heated, for example, benzoyl peroxide or the like is blended in advance in the liquid and/or the powder.

In the case of using ultraviolet rays, a suitable amount of a widely-known ultraviolet polymerization initiator (for example, benzoin methyl ether, etc.) is added to the liquid in advance. In this case, for producing a dental structural material, the liquid to be used can be selected without any particular limitation as long as it is field proven in ultraviolet polymerization for dentistry.

Instead of the partial beam irradiation, the entire area also can be irradiated with the beam at one time. In this case, the polymerization initiator is blended only in the liquid, and an operation similar to that for photopolymerization described above is carried out.

Of course, plural polymerization methods that have been used conventionally as a method for polymerizing and curing resin materials also can be used in combination. For example, by combining photopolymerization and chemical polymerization, the part that light does not reach is cured by the chemical polymerization, and a vicinity of the surface, which has lower polymerizability in general when the chemical polymerization is adopted, is cured sufficiently by the photopolymerization. In this way, the disadvantage of one of the polymerization methods can be complemented by the other's advantage, and vice versa.

[Computer]

The layered-object forming apparatus includes a computer in order to store and compute various kinds of information and control an operation of each of the elements constituting the layered-object forming apparatus. As its hardware, a general personal computer that is widespread can be used. It is preferable that its software includes a function of storing, editing, holding and retaining the shape of a three-dimensional structure to be obtained, a computing function for using different materials in their suitable ways, a function of generating control data of the individual elements constituting the layered-object forming apparatus based on the shape data, and a function of controlling the individual elements according to the generated control data and producing the three-dimensional structure automatically.

The computer may be used for generating three-dimensional shape data of a three-dimensional structure to be obtained. For example, by measuring the shape of a pre-produced model or using a CAD, it is possible to generate the shape data. Of course, it also is possible to generate the shape data by editing shape measurement data with a CAD or other software.

The three-dimensional measuring unit 50 may be utilized for measuring the shape. For example, the base 12 may be placed on the forming table 10, and the shape of a surface on which a three-dimensional structure is to be formed may be measured using the three-dimensional measuring unit 50. These measurement data can be utilized for generating the three-dimensional shape data of the three-dimensional structure to be obtained.

Internal structure data may be added to the three-dimensional shape data. Also, data concerning color tones and physical properties may be added. At this time, the color tones and physical properties do not have to be uniform over the entire three-dimensional structure but may differ from one part to another. Furthermore, the color tones and physical properties may be varied sequentially by gradation. When determining the color tone of each part, it also may be possible to use data of a mechanical colorimeter. The selection and delivery amount of the liquid are computed and added to liquid delivery control data so that the set color tone can be reproduced.

The three-dimensional shape data generated in this manner are cut along a plurality of horizontal planes at a certain pitch, thereby generating liquid delivery control data. At this time, the pitch is set to be the same as the height of one layer. Depending on the combination of the liquid and the powder to be used, expansion or shrinkage occurs due to swelling and chemical reaction, etc. By taking the above into consideration, the amount of the liquid and powder to be applied for forming one consolidated portion layer is determined.

The computer controls the position of the liquid feeder 20 and the delivery of the liquid based on the liquid delivery control data for the respective layers.

In order to layer the powder with the accuracy and speed that are needed, it is preferable that the computer also controls the movement of the powder feeder 30, the initiation and cessation of the falling of the powder and the supply of the powder from the powder reservoir tank to the powder feeder 30.

The computer further may have a function of exchanging necessary data via a network, a function of processing the data from the three-dimensional measuring unit 50, a function of monitoring the state of each part, and a safety function of issuing an alarm or making an emergency shut down of the operation of each element as necessary.

[After Treatment]

The surface of the obtained three-dimensional structure 60 that has contacted the base 12 truly reflects the surface shape of the base 12. When the surface of the base 12 is smooth, a surface that has contacted this surface has extremely small steps due to layering and minute irregularities due to the powder. It should be noted that a further surface finishing treatment may be carried out as necessary. Further, in order to remove the steps due to layering and minute irregularities that are formed on surfaces other than the surface of the three-dimensional structure 60 that has contacted the base 12, various surface finishing treatments may be carried out.

In order to remove the steps due to layering and the irregularities, it is preferred to use a method of applying a step remover so as to fill the steps and irregularities and finishing the surface by grinding and abrasion, a method of immersing the three-dimensional structure in a liquid containing a step remover, lifting it up and finishing the surface by grinding and abrasion, a method of allowing an ultrasonic vibrator to contact the part having the steps and irregularities so as to cause partial melting and smoothing of the surface, followed by abrasion finishing, or the like.

As the step remover, desirably, the mixture of the powder and the liquid that are of similar kinds to those used for forming is used as a basic composition and its flowability and thixotropy are adjusted to optimal values according to the purposes.

Moreover, if necessary, an immersion treatment into a surface lubricant and abrasion may be performed, thereby removing the steps and irregularities and providing a surface lubricity.

(Embodiment 2)

Figure 4:
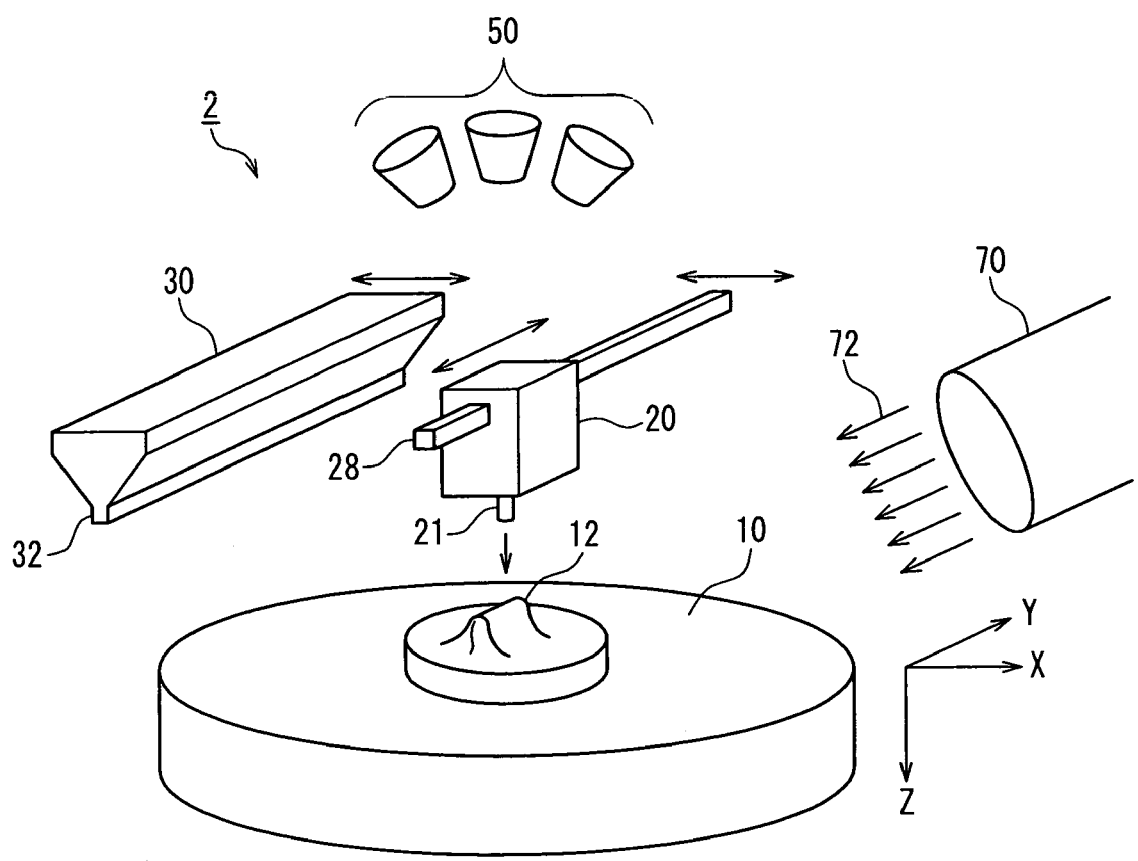
FIG. 4 is a perspective view showing a schematic configuration of a layered-object forming apparatus according to Embodiment 2 of the present invention.

FIG. 4 is a perspective view showing a schematic configuration of a layered-object forming apparatus 2 according to Embodiment 2 of the present invention. Constituent elements that are the same as those in FIG. 1 are assigned the same reference numerals, and the detailed description thereof will be omitted.

The following description mainly is directed to points of Embodiment 2 that are different from Embodiment 1.

The layered-object forming apparatus 2 according to Embodiment 2 has an air nozzle 70 that ejects a gas 72 toward the base 12 on the forming table 10, instead of the arm 40 of the layered-object forming apparatus 1 according to Embodiment 1 for flipping the forming table 10.

In order to remove surplus powder that has not been consolidated by the liquid, the forming table 10 has been flipped so as to allow the powder to fall as shown in FIG. 3C in Embodiment 1. In contrast, in Embodiment 2, the gas 72 is ejected from the air nozzle 70 toward the base 12, thereby blowing off and removing the surplus powder by a gas pressure.

The position of the air nozzle 70 and the direction in which the gas 72 is ejected may be variable so that the gas 72 is ejected to an overall surface of the base 12.

The forming table 10 may be provided with a vibration generating device 19 that vibrates the forming table 10. By ejecting the gas 72 while vibrating the forming table 10, it is possible to remove the surplus powder easily within a short time.

Embodiment 2 is similar to Embodiment 1 except that the method for removing the surplus powder is different from that in Embodiment 1, and thus produces an effect similar to Embodiment 1.

Incidentally, it also may be possible to blow off and remove the surplus powder 34 using the air nozzle 70 illustrated in Embodiment 2 while the forming table 10 is flipped as shown in FIG. 3C in Embodiment 1. This allows more nearly complete removal of the surplus powder.

(Embodiment 3)

Figure 5:
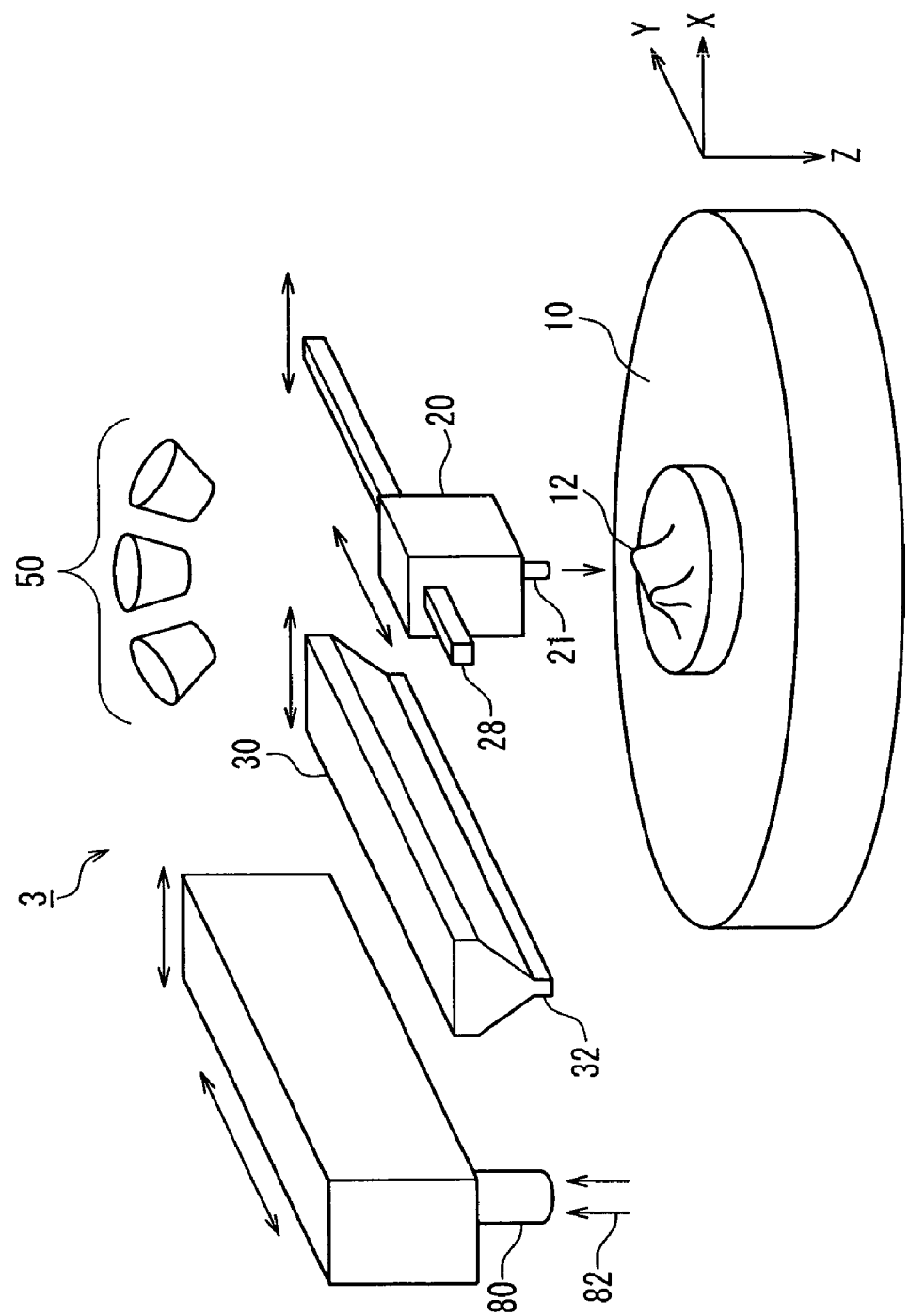
FIG. 5 is a perspective view showing a schematic configuration of a layered-object forming apparatus according to Embodiment 3 of the present invention.

FIG. 5 is a perspective view showing a schematic configuration of a layered-object forming apparatus 3 according to Embodiment 3 of the present invention. Constituent elements that are the same as those in FIG. 1 are assigned the same reference numerals, and the detailed description thereof will be omitted.

The following description mainly is directed to points of Embodiment 3 that are different from Embodiment 1.

The layered-object forming apparatus 3 according to Embodiment 3 has a suction nozzle 80 that sucks an atmosphere 82 surrounding the base 12 on the forming table 10, instead of the arm 40 of the layered-object forming apparatus 1 according to Embodiment 1 for flipping the forming table 10.

In order to remove surplus powder that has not been consolidated by the liquid, the forming table 10 has been flipped so as to allow the powder to fall as shown in FIG. 3C in Embodiment 1. In contrast, in Embodiment 3, the surplus powder together with the atmosphere 82 is sucked into the suction nozzle 80 and removed.

The position of the suction nozzle 80 and the direction in which the atmosphere 82 is sucked may be variable so that the atmosphere 82 can be sucked from an overall surface of the base 12.

The forming table 10 may be provided with a vibration generating device 19 that vibrates the forming table 10. By sucking the surplus powder while vibrating the forming table 10, it is possible to remove the surplus powder easily within a short time.

Embodiment 3 is similar to Embodiment 1 except that the method for removing the surplus powder is different from that in Embodiment 1, and thus produces an effect similar to Embodiment 1.

Incidentally, it also may be possible to suck and remove the surplus powder 34 using the suction nozzle 80 illustrated in Embodiment 3 while the forming table 10 is flipped as shown in FIG. 3C in Embodiment 1. This allows more nearly complete removal of the surplus powder.

Further, the surplus powder may be blown off using the air nozzle 70 illustrated in Embodiment 2, and at the same time, the scattered powder may be sucked by the suction nozzle 80 illustrated in Embodiment 3.

Moreover, it also may be possible to blow off the surplus powder using the air nozzle 70 illustrated in Embodiment 2 while the forming table 10 is flipped as shown in FIG. 3C in Embodiment 1, and at the same time, the scattered powder may be sucked by the suction nozzle 80 illustrated in Embodiment 3.

(Embodiment 4)

Figure 6:
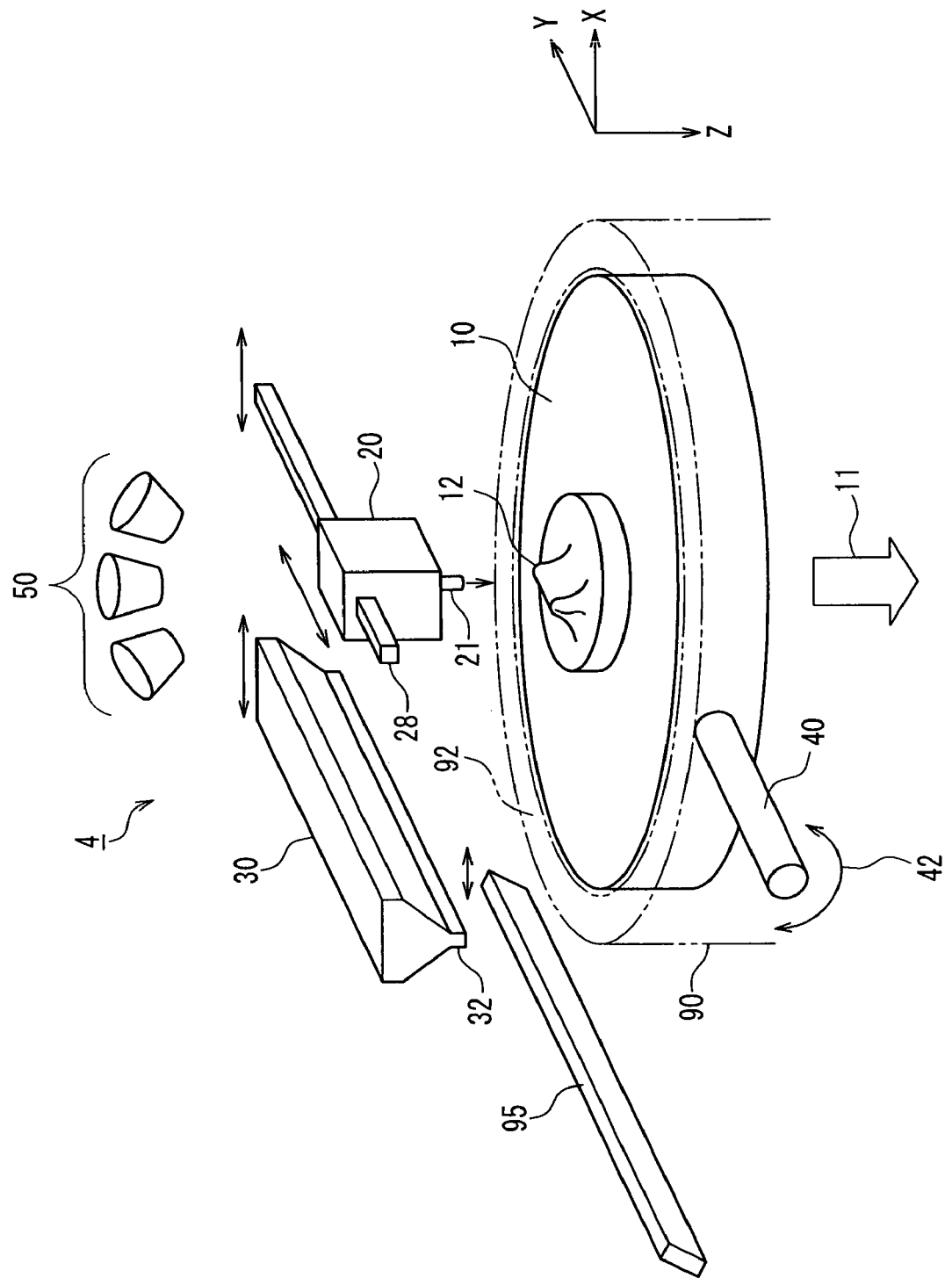
FIG. 6 is a perspective view showing a schematic configuration of a layered-object forming apparatus according to Embodiment 4 of the present invention.

FIG. 6 is a perspective view showing a schematic configuration of a layered-object forming apparatus 4 according to Embodiment 4 of the present invention. Constituent elements that are the same as those in FIG. 1 are assigned the same reference numerals, and the detailed description thereof will be omitted.

The following description mainly is directed to points of Embodiment 4 that are different from Embodiment 1.

The layered-object forming apparatus 4 according to Embodiment 4 is provided with a container 90 including a wall surrounding the horizontal periphery of the forming table 10 and a leveling member 95 that slides over an upper surface 92 of the container 90 parallel with the horizontal plane in the X-axis direction. Also, the forming table 10 is lowered at a constant pitch while being made to slide on an internal wall surface of the container 90 by a driving mechanism, which is not shown in the figure. The powder feeder 30 has a powder dispersion width that is substantially the same as the dimension of the forming table 10 in the Y-axis direction. The powder feeder 30 moves in the X-axis direction while dispersing the powder, so that the powder is dispersed on an overall surface of the forming table 10. In FIG. 6, for easier understanding of the structure, the container 90 is indicated by chain double-dashed lines so that the forming table 10 therein is seen through it.

The method for producing a three-dimensional structure using the above-described layered-object forming apparatus 4 will be explained with reference to FIGS. 7A to 7C and FIGS. 8A to 8C.

Figure 7A:
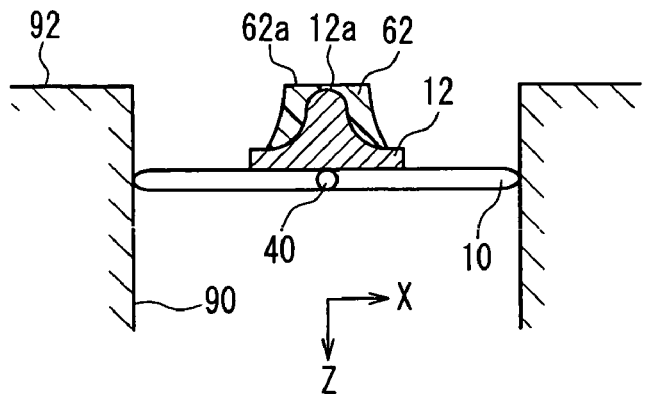
FIG. 7A is a sectional view showing a process in a method for producing a three-dimensional structure using the layered-object forming apparatus according to Embodiment 4 of the present invention.

First, a lower structure 62 in which a plurality of consolidated portion layers that are formed by consolidation of the liquid and the powder are formed on the base 12 is produced as shown in FIG. 7A by the method described in Embodiment 1. Here, a top portion 12a of the base 12 is covered completely with the lower structure 62, and an upper surface 62a of the lower structure 62 is at the same height as the upper surface 92 of the container 90.

Figure 7B:
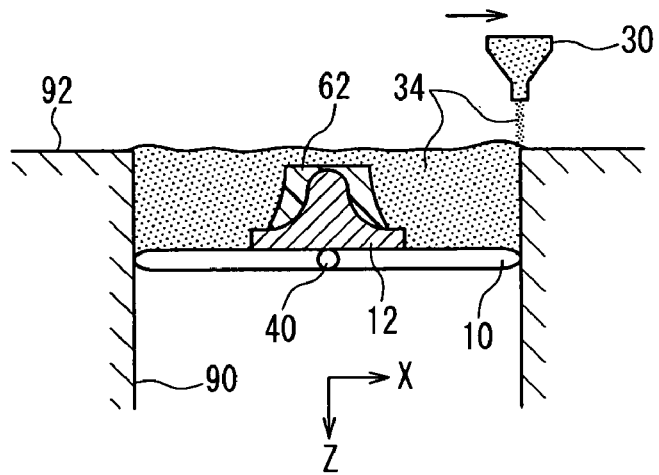
FIG. 7B is a sectional view showing a process in the method for producing a three-dimensional structure using the layered-object forming apparatus according to Embodiment 4 of the present invention.

Next, the forming table 10 is lowered relative to the container 90 by a unit pitch in the Z-axis direction. Then, as shown in FIG. 7B, the powder 34 is dispersed from the powder feeder 30 into the container 90 to such an extent that the lower structure 62 is buried completely.

Figure 7C:
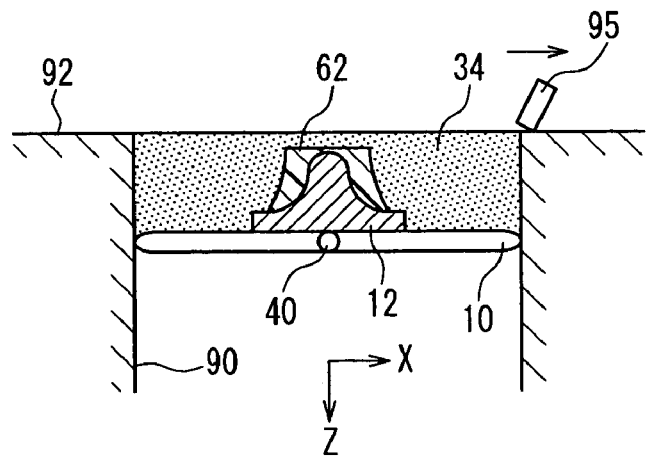
FIG. 7C is a sectional view showing a process in the method for producing a three-dimensional structure using the layered-object forming apparatus according to Embodiment 4 of the present invention.

Subsequently, as shown in FIG. 7C, the leveling member 95 is moved in the X-axis direction while an lower end thereof is kept in contact with the upper surface 92 of the container 90. As a result, the upper surface of the powder 34 is restricted to be at the same height as the upper surface 92 of the container 90. In this manner, a powder layer with a uniform thickness is formed on the lower structure 62. The powder that is removed by the leveling member 95 falls on a collection tray, which is not shown in the figure, and is collected.

Figure 8A:
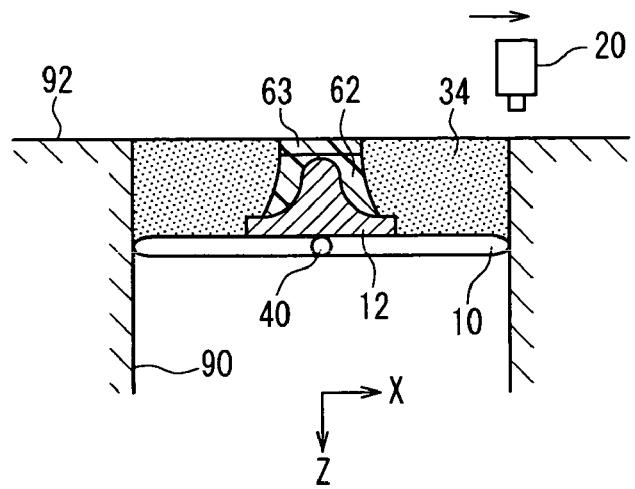
FIG. 8A is a sectional view showing a process in the method for producing a three-dimensional structure using the layered-object forming apparatus according to Embodiment 4 of the present invention.

Thereafter, as shown in FIG. 8A, the liquid is delivered toward the powder 34 at predetermined positions while the liquid feeder 20 is moved. In the part to which the liquid is applied, the liquid causes the powder 34 to swell and is polymerized, so that the liquid and the powder are consolidated to form a consolidated portion 63. The consolidated portion 63 also is integrated with the lower structure 62.

Next, the forming table 10 is lowered relative to the container 90 by a unit pitch in the Z-axis direction. Then, processes similar to those from FIG. 7A to FIG. 8A described above are repeated necessary times, thus layering sequentially the consolidated portion layers formed by consolidation of the liquid and the powder on the lower structure 62. The position at which the liquid is applied by the liquid feeder 20 can be varied to vary the shape of each of the consolidated portion layers.

Figure 8B:
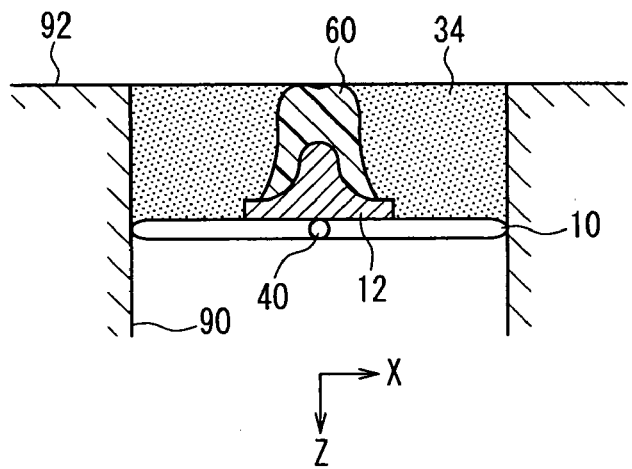
FIG. 8B is a sectional view showing a process in the method for producing a three-dimensional structure using the layered-object forming apparatus according to Embodiment 4 of the present invention.
Figure 8C:
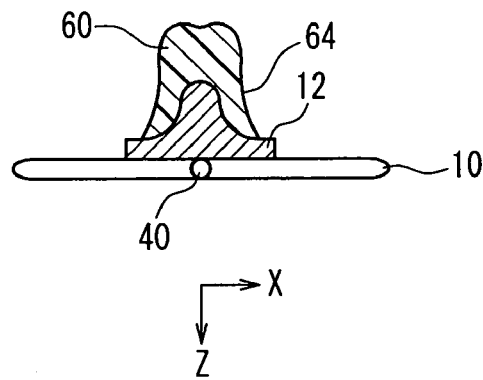
FIG. 8C is a sectional view showing a process in the method for producing a three dimensional structure using the layered-object forming apparatus according to Embodiment 4 of the present invention.

After the consolidated portion layers are formed up to the top portion of the three-dimensional structure 60 to be obtained as shown in FIG. 8B, the forming table 10 is flipped via the arm 40. In this manner, the unconsolidated surplus powder 34 on the forming table 10 falls by gravity and is removed. Consequently, as shown in FIG. 8C, the three-dimensional structure 60 made of a large number of the consolidated portion layers that are formed by the consolidation of the liquid and the powder can be formed on the base 12.

Similarly to Embodiment 1, the finished shape of the three-dimensional structure 60 on the forming table 10 may be measured using the three-dimensional measuring unit 50.

Thereafter, the three-dimensional structure 60 is separated from the base 12, thus obtaining the three-dimensional structure 60 with a desired shape. If necessary, a surface finishing treatment may be carried out so as to improve a surface lubricity.

In the present embodiment, until the top portion of the base 12 is covered, the lower structure 62 is formed by repeating the processes of FIGS. 3A to 3C illustrated in Embodiment 1, and then, the processes of FIGS. 7A to 8A illustrated in the present embodiment are repeated, thereby completing the three-dimensional structure 60. Since the liquid and the powder are consolidated by applying the liquid at desired positions after filling the powder 34 in the container 90 as in the processes of FIGS. 7A to 8A, it is easy to produce the three-dimensional structure 60 with a complex shape such as a shape having an undercut (a portion in the side wall that is recessed from the upper portion) 64 shown in FIG. 8C.

In the above-described example, the surplus powder 34 has been removed after the process of FIG. 8B by flipping the forming table 10. However, the surplus powder 34 may be blown off and removed by a gas pressure by ejecting the gas toward the powder 34 as illustrated in Embodiment 2, or the surplus powder 34 together with the gas may be sucked and removed as illustrated in Embodiment 3. Alternatively, the surplus powder 34 may be removed by combining these methods. Furthermore, at the time of removing the surplus powder 34, the forming table 10 may be vibrated by a vibration generating device 19.

In the example described above, the forming table 10 has been lowered relative to the container 90 by a predetermined pitch. However, the height of the forming table 10 may be fixed, and the container 90 may be lifted by a predetermined pitch. Alternatively, the table 10 and the container 90 may be moved in opposite directions along the Z axis.

The thickness of one of the consolidated portion layers formed on the lower structure 62 varies depending on a relative movement pitch between the container 90 and the forming table 10 in the Z-axis direction. The layer thickness (namely, the movement pitch) can be changed according to the intended use of a three-dimensional structure. A decrease in the layer thickness raises the resolution and improves a dimensional accuracy and a surface smoothness.

Depending on the combination of the liquid and the powder to be used, expansion or shrinkage occurs due to swelling and chemical reaction, etc. By taking the above into consideration, the relative movement pitch of the forming table 10 in the Z-axis direction is set.

In the example described above, after the powder feeder 30 is moved along the X axis, the leveling member 95 has been moved along the X axis. However, the leveling member 95 may be attached integrally to the powder feeder 30 on the downstream side in the movement direction, thereby carrying out the operation of FIG. 7B and the operation of FIG. 7C at the same time. Alternatively, the leveling member 95 may be attached to the powder feeder 30 on both sides in the movement direction. In this case, when the powder feeder 30 is moved in either direction along the X axis, it is possible to carry out the operation of FIG. 7B and that of FIG. 7C at the same time at one movement.

(Embodiment 5)

Figure 9:
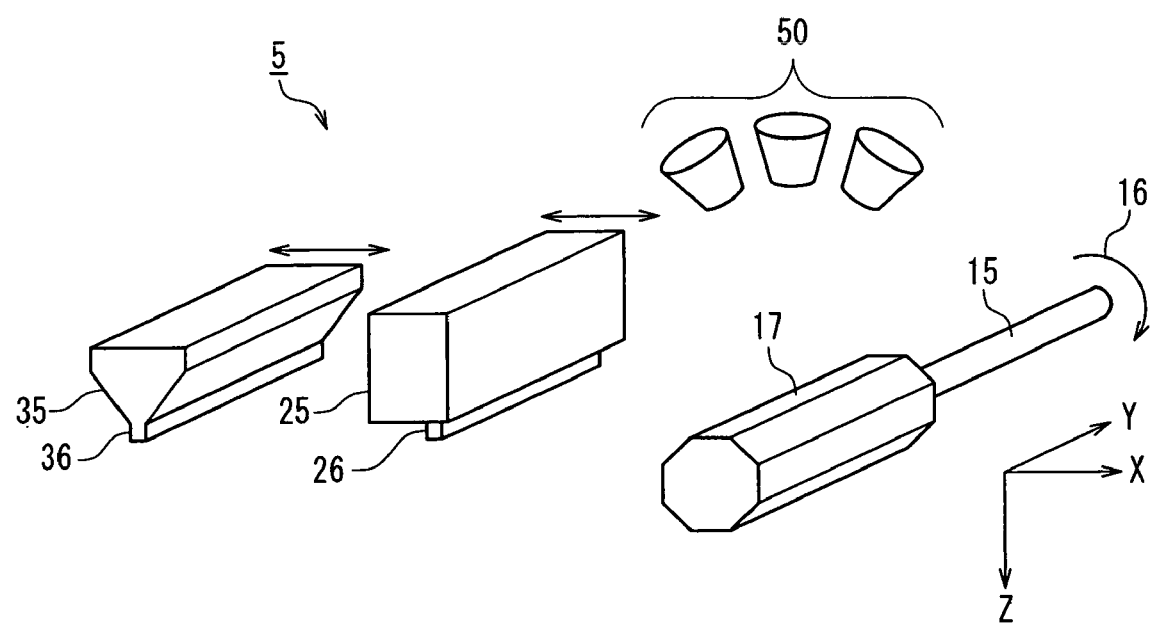
FIG. 9 is a perspective view showing a schematic configuration of a layered-object forming apparatus according to Embodiment 5 of the present invention.

FIG. 9 is a perspective view showing a schematic configuration of a layered-object forming apparatus 5 according to Embodiment 5 of the present invention. As shown in the figure, horizontal axes that are perpendicular to each other are indicated by an axis an X axis and a Y axis, and a vertical axis is indicated by a Z axis.

One end of a rod-like member (a holding mechanism) 15 whose longitudinal direction corresponds to a Y-axis direction is inserted to a base 17, whereby the base 17 is held. A three-dimensional structure is layered and formed on the base 17. A rotation driving mechanism, which is not shown in the figure, is coupled to the other end of the rod-like member 15, and the rod-like member 15 and the base 17 are rotated in a direction indicated by an arrow 16.

A liquid feeder (a liquid applying device) 25 delivers a liquid from above the base 17 and allows the liquid to fall. On a lower surface of the liquid feeder 25, a plurality of delivery nozzles 26 are aligned in the Y-axis direction at least over the dimension of the base 17 in the Y-axis direction. The plurality of delivery nozzles 26 are controlled independently from one another and allow the liquid to fall downward. The liquid feeder 25 is driven in an X-axis direction by a driving mechanism, which is not shown in the figure. In other words, the liquid feeder 25 is capable of moving to a position above the base 17 and allowing the liquid to fall at desired positions in the Y-axis direction from above the base 17.

A powder feeder (a powder applying device) 35 has a powder dispersion width that is at least equal to or greater than the dimension of the base 17 in the Y-axis direction. The powder feeder 35 is driven in the X-axis direction by a driving mechanism, which is not shown in the figure. In other words, the powder feeder 35 is capable of moving to a position above the base 17 and allowing the powder to fall from above the base 17.

A three-dimensional measuring unit 50 is provided above the base 17.

The method for producing a three-dimensional structure using the above-described layered-object forming apparatus 5 will be explained.

First, as shown in FIG. 9, the base 17 is fixed onto the rod-like member 15. For example, in the case of producing a crownwork, for example, a crown, a bridge, a frame or the like, the base 17 is a replica of the shape of a patient's abutment.

At this time, the base 17 may be positioned accurately on the rod-like member 15 using the three-dimensional measuring unit 50. Also, while rotating the rod-like member 15 and the base 17 in the direction indicated by the arrow 16, it also may be possible to measure an external shape of the base 17 using the three-dimensional measuring unit 50.

Figure 10A:
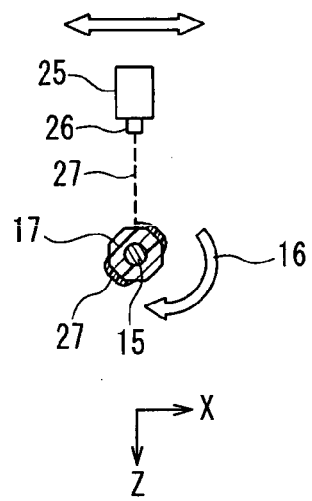
FIG. 10A shows a process in a method for producing a three-dimensional structure using the layered-object forming apparatus according to Embodiment 5 of the present invention.

Next, as shown in FIG. 10A, the liquid feeder 25 is moved to a position above the base 17, and then a liquid 27 is allowed to fall downward from the plurality of delivery nozzles 26 while the rod-like member 15 and the base 17 are rotated in the direction indicated by the arrow 16. At this time, the plurality of delivery nozzles 26 of the liquid feeder 25 are controlled independently from one another in synchronization with the rotation of the base 17. Consequently, the liquid 27 is made to adhere to only the desired positions on an external surface of the base 17.

Figure 10B:
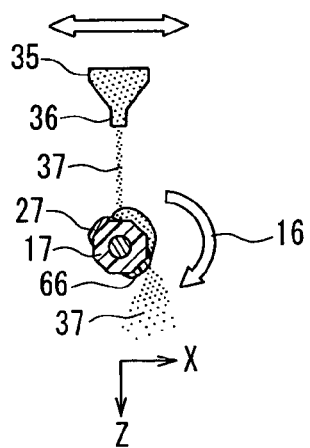
FIG. 10B shows a process in the method for producing a three-dimensional structure using the layered-object forming apparatus according to Embodiment 5 of the present invention.

When the adhesion of the liquid 27 is finished through one turn of the base 17, the liquid feeder 25 is retracted, and the powder feeder 35 is moved to a position above the base 17. Then, as shown in FIG. 10B, while the rod-like member 15 and the base 17 are rotated in the direction indicated by the arrow 16, powder 37 is allowed to fall downward from a slit 36 of the powder feeder 35. At this time, in the part to which the liquid 27 adheres in the process of FIG. 10A, the liquid 27 causes the powder 37 to swell and is polymerized, so that the liquid and the powder are consolidated to form a consolidated portion 66. The powder 37 that has fallen in the part to which no liquid adheres falls by gravity when the base 17 is rotated, and is removed. After one turn of the base 17, the slit 36 is closed so as to stop dispersing the powder 37, and then the powder feeder 35 is retracted.

Figure 10C:
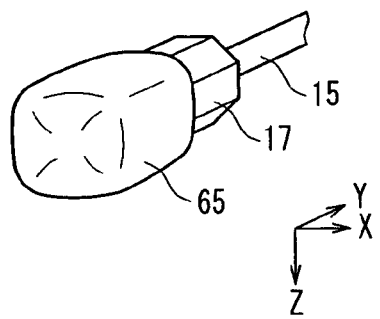
FIG. 10C shows a process in the method for producing a three-dimensional structure using the layered-object forming apparatus according to Embodiment 5 of the present invention.

Processes similar to those from FIG. 10A to FIG. 10B are repeated the necessary number of times, thus layering sequentially the consolidated portion layers formed by consolidation of the liquid and the powder on the base 17. The position at which the liquid is applied by the liquid feeder 25 can be varied to vary the position at which each of the consolidated portion layers is formed. Consequently, as shown in FIG. 10C, a three-dimensional structure 65 made of a large number of the consolidated portion layers that are formed by the consolidation of the liquid and the powder can be formed on the base 17.

The finished shape of the three-dimensional structure 65 on the rod-like member 15 may be measured using the three-dimensional measuring unit 50.

Thereafter, the three-dimensional structure 65 is separated from the base 17, thus obtaining the three-dimensional structure 65 with a desired shape. If necessary, a surface finishing treatment may be carried out so as to improve a surface lubricity.

Similarly to Embodiment 1, in the present embodiment, the liquid also is applied first on the base 17. Then, the powder is dispersed, followed by consolidating the liquid and the powder. In other words, not the powder but the liquid is applied first on the surface of the base 17. Therefore, the surface of the base 17 is transferred substantially truly on the surface that has contacted the base 17 of the finished three-dimensional structure 65. Consequently, when the surface of the base 17 is made smooth in advance, it is possible to achieve a smooth surface similar thereto.

For example, in the case of producing a crownwork such as a crown, a bridge or a frame, when the base 17 that reproduces the shape of a patient's abutment is used, the surface to be in contact with the abutment can be made smooth. Thus, it is possible to omit or simplify a surface smoothing treatment of this surface. Also, since deterioration of the dimensional accuracy caused by the surface smoothing treatment can be reduced, the adaptability is not degraded. In this manner, it is possible to produce a dental structural material highly accurately within a short time without the work of a highly skilled worker.

In the present invention, the layer thickness (the thickness of one consolidated portion) can be varied according to the purpose of the three-dimensional structure. A smaller layer thickness increases the resolution, resulting in improvement in the dimensional accuracy and the surface smoothness.

The arm 40 of the layered-object forming apparatus 1 illustrated in Embodiment 1 may be used as the rod-like member 15 in Embodiment 5. In other words, in the layered-object forming apparatus 1 illustrated in Embodiment 1, the forming table 10 attached to the tip of the arm 40 is made detachable. According to a three-dimensional structure to be produced, the forming table 10 is replaced with the base 17. At this time, an appropriate connection member may be interposed between the arm 40 and the base 17. This makes it possible to produce a large structure such as a complete denture using the forming table 10 and produce a small structure such as a crownwork using the base 17. Therefore, three-dimensional structures of various sizes can be produced with a common layered-object forming apparatus.

In the present invention, the materials for the bases 12 and 17 are not particularly limited and can be gypsum, for example. It is preferable that a mold release agent such as vaseline is applied to the surfaces of the bases 12 and 17 so that the liquids 22 and 27 are prevented from permeating through those surfaces and the three-dimensional structures 60 and 65 can be separated easily. Also, in the case of producing a crownwork or the like, it is preferable that a dental spacer is applied to the surfaces of the bases 12 and 17 in order to secure a cement layer (an adhesive layer) between the crownwork and the patient's abutment.

(Embodiment 6)

Figure 11:
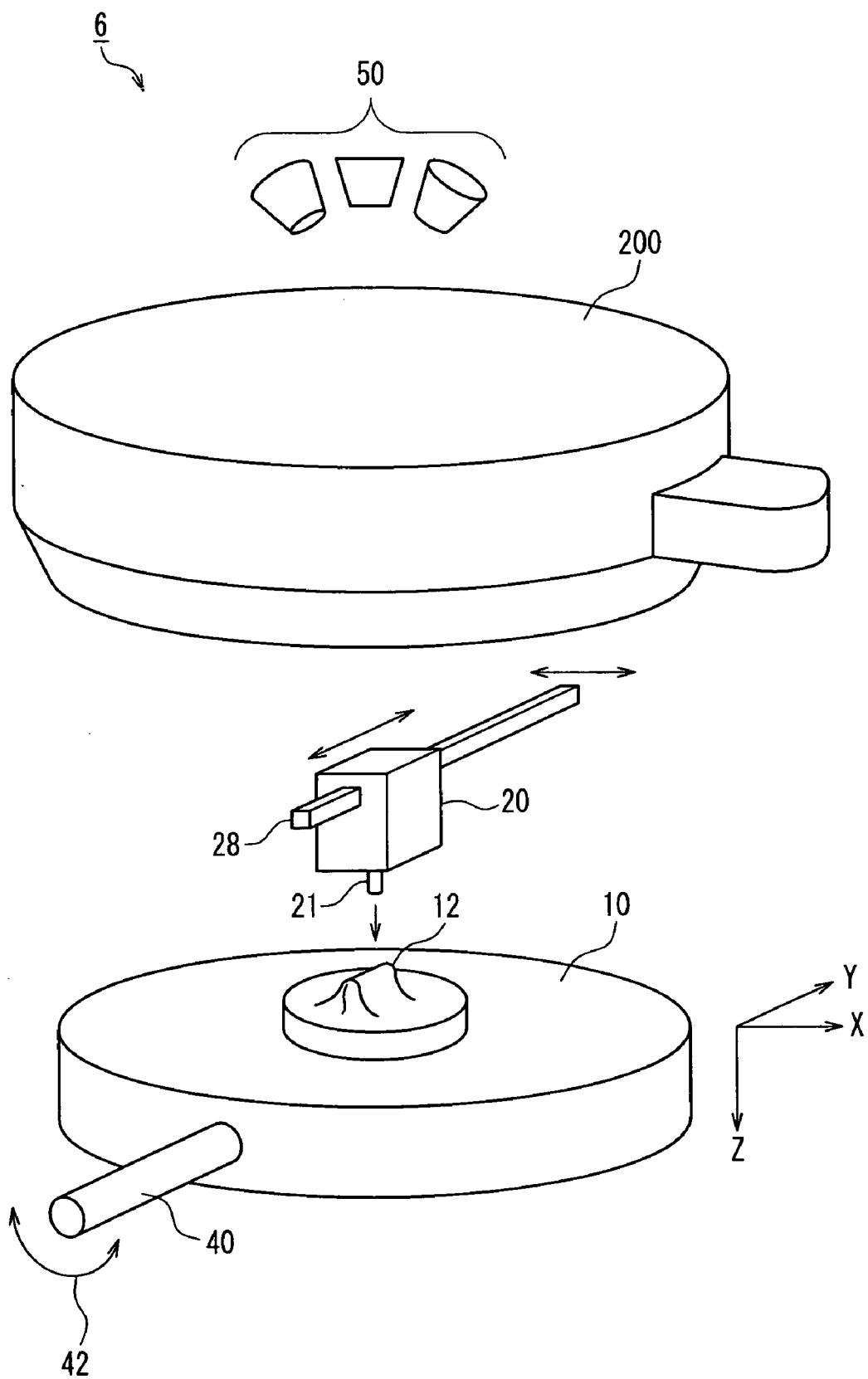
FIG. 11 is a perspective view showing a schematic configuration of a layered-object forming apparatus according to Embodiment 6 of the present invention.

FIG. 11 is a perspective view showing a schematic configuration of a layered-object forming apparatus 6 according to Embodiment 6 of the present invention. Constituent elements that are the same as those in FIG. 1 are assigned the same reference numerals, and the detailed description thereof will be omitted.

The following description mainly is directed to points of Embodiment 6 that are different from Embodiment 1.

The layered-object forming apparatus 6 according to Embodiment 6 has a multilayer screen powder feeder (in the following, simply referred to as a "powder feeder") 200, instead of the powder feeder 30 of the layered-object forming apparatus 1 according to Embodiment 1.

One or both of the three-dimensional measuring unit 50 and the powder feeder 200 can be moved in a direction parallel with a plane including the X axis and the Y axis (an XY plane) and can be arranged above the forming table 10 or retracted from the position above the forming table 10 as necessary. Together with the uniaxial guiding mechanism 28 that drives the liquid feeder 20 in the Y-axis direction, one or both of the three-dimensional measuring unit 50 and the powder feeder 200 may be driven in the X-axis direction by a driving mechanism, which is not shown in the figure.

Figure 12:
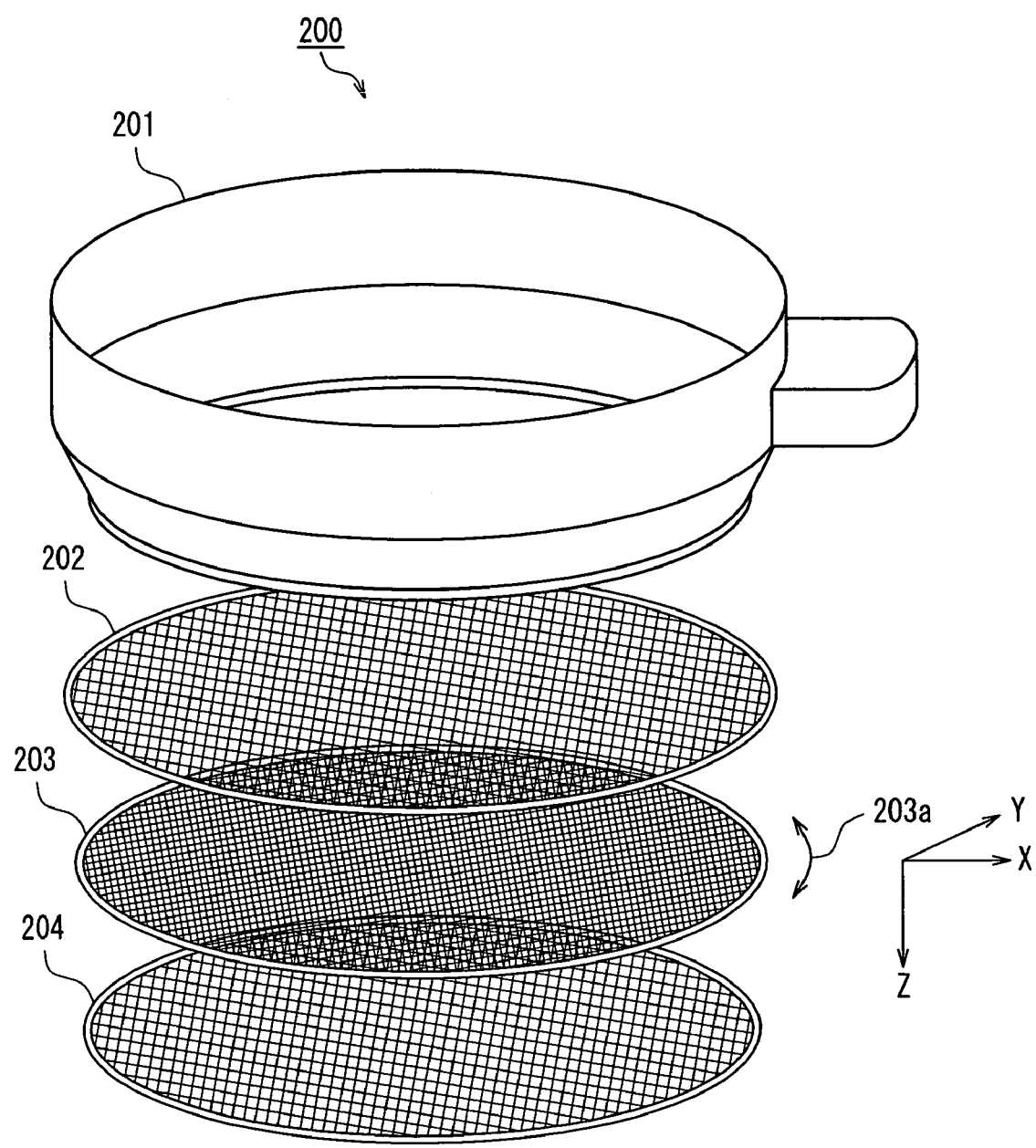
FIG. 12 is an exploded perspective view showing a multilayer screen powder feeder in the layered-object forming apparatus according to Embodiment 6 of the present invention.

FIG. 12 is an exploded perspective view showing the powder feeder 200. The powder feeder 200 includes a powder reservoir 201 and three circular screens 202, 203 and 204. The powder reservoir 201 is a substantially-cup-shaped container for storing powder to be dispersed on the base 12, and a lower surface thereof is provided with a circular opening. The screens 202, 203 and 204 are stacked in this order along the Z-axis direction and attached to the powder reservoir 201 so as to block the opening on the lower surface of the powder reservoir 201. Each of the screens 202, 203 and 204 is provided with a large number of minute through holes (in the following, referred to as "minute holes") through which the powder can pass.

Among the screens 202, 203 and 204, the upper screen 202 and the lower screen 204 are stationary screens that are fixed to the powder reservoir 201, and the middle screen 203 is a driven screen that is rotationally-driven in the XY plane in directions indicated by arrows 203a. A driving source for rotating the screen 203 is not particularly limited and can be, for example, a motor, a spring, a pendulum or the like. The screen 203 may be connected to its driving source directly or via a power transmission mechanism such as a reduction gear. Furthermore, the screen 203 and its driving source may be arranged close to each other or away from each other. When they are arranged away from each other, a driving force of the driving source can be transmitted to the screen 203 via a link mechanism, a chain belt or the like.

When the middle screen 203 is stationary, the powder in the powder reservoir 201 does not pass through and fall below the screens 202, 203 and 204. On the other hand, when the screen 203 is rotated, the powder passes through the respective minute holes of the screens 202, 203 and 204 and falls below the screens 202, 203 and 204. Thereafter, when the rotation of the screen 203 is stopped, the powder stops falling. In other words, the screens 202, 203 and 204 can control the falling of the powder in the powder reservoir 201 onto the forming table 10.

Similarly to Embodiment 1, after the liquid is applied to the base 12 by the liquid feeder 20, the liquid feeder 20 is retracted from the position above the forming table 10. Then, the powder feeder 200 is moved to the position above the forming table 10, and the powder is dispersed on the base 12.

In each of the screens 202, 203 and 204, an area in which a large number of the minute holes are formed is larger than the upper surface of the forming table 10. Thus, once the powder feeder 200 is moved to the position above the forming table 10, simply by rotating the screen 203, it is possible to disperse the powder over an entire surface of the forming table 10. In other words, in order to disperse the powder over the entire surface of the forming table 10, it has been necessary to move the powder feeder 30 in the X-axis direction in Embodiment 1, but the powder feeder 200 does not have to be moved in the present embodiment. Also, for controlling the dispersion of the powder, it has been necessary to control the opening and closing of the slit 32 in Embodiment 1, but it is sufficient to control the rotation of the screen 203 in the present embodiment. As described above, in the present embodiment, the powder can be dispersed over a large area at one time. Moreover, the dispersion of the powder can be controlled by a simple mechanism.

After a necessary amount of the powder is dispersed, the rotational movement of the screen 203 is stopped so as to stop dispersing the powder.

The rotational motion of the screen 203 may be a continuous rotation in only one direction or an inversion motion whose rotational direction changes. Alternatively, the screen 203 may make a reciprocating motion along one direction parallel with the XY plane instead of the rotational motion.

The opening diameter of the minute holes formed in each of the screens 202, 203 and 204 preferably is at least twice and particularly preferably is at least six times as large as the maximum diameter of particles contained in the powder to be used.

Figure 13A:
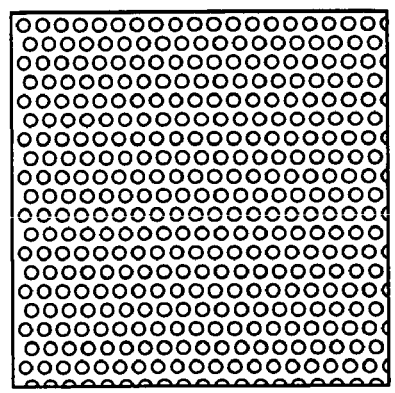
FIG. 13A is a plan view showing an example of minute holes formed in a screen in the multilayer screen powder feeder in the layered-object forming apparatus according to Embodiment 6 of the present invention.
Figure 13B:
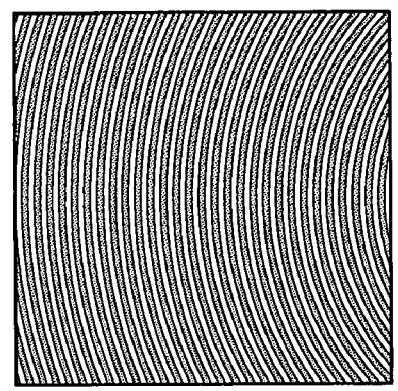
FIG. 13B is a plan view showing another example of the minute holes formed in the screen in the multilayer screen powder feeder in the layered-object forming apparatus according to Embodiment 6 of the present invention.
Figure 13C:
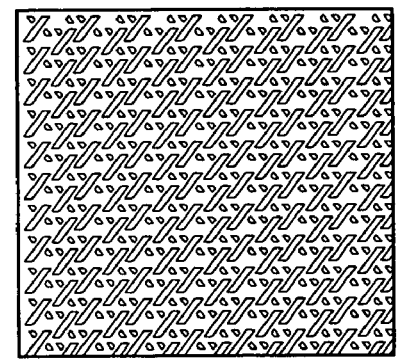
FIG. 13C is a plan view showing yet another example of the minute holes formed in the screen in the multilayer screen powder feeder in the layered-object forming apparatus according to Embodiment 6 of the present invention.
Figure 13D:
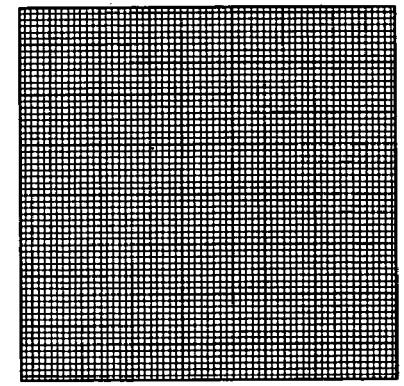
FIG. 13D is a plan view showing yet another example of the minute holes formed in the screen in the multilayer screen powder feeder in the layered-object forming apparatus according to Embodiment 6 of the present invention.

The opening shape of the minute holes formed in each of the screens 202, 203 and 204 is not particularly limited as long as it is possible to control the falling of the powder as described above. For example, instead of the circular shape as shown in FIG. 13A, an elliptical shape, a rectangular shape, various polygons or a slit may be used. Alternatively, any of a circular arc shape as shown in FIG. 13B, a combination of plural kinds of openings with different shapes as shown in FIG. 13C and a mesh formed by a large number of wires extending in longitudinal and transverse directions as shown in FIG. 13D may be adopted. Also, the opening ratio (the ratio of a total area of the minute holes with respect to a unit area of the screen) and the number of minute holes are not particularly limited, either, as long as it is possible to control the falling of the powder as described above.

The screens 202, 203 and 204 may be an impeller-like member formed of a plurality of plate members that are spaced away from each other, instead of the above-described member having a large number of minute holes. In this case, the number, shape, dimension, etc. of the plate members are not particularly limited as long as it is possible to control the falling of the powder as described above.

The screens 202, 203 and 204 may be identical with or different from each other.

Although FIG. 12 has illustrated an example in which the powder feeder 200 includes three screens 202, 203 and 204, the number of the screens is not limited to three. A smaller number of the screen makes the structure simpler, so that clogging does not occur easily, thus allowing easy cleaning, and the screen replacement is easy. Although a larger number of the screen makes it difficult to achieve these advantages, less powder leakage occurs when the driven screen is stopped, thus improving the controllability of initiation and cessation of the powder dispersion. In the present invention, the number of the screens needs to be at least two. The upper limit thereof is not particularly limited but preferably is equal to or smaller than six in practice. Among the plurality of screens, the driven screen and the non-driven screen preferably are arranged alternately.

The adjacent screens may be in contact with or spaced away from each other. When they are in contact with each other, the contact pressure thereof can be set freely in a practical range. By adjusting the distance and contact pressure of the adjacent screens, it is possible to adjust the dispersion amount of the powder, the controllability of initiation and cessation of the dispersion, the powder leakage when the driven screen is stopped, etc.

The material for the screens is not particularly limited and can be selected suitably from metal, paper, glass, fabric, plastics and the like, for example. Also, according to the purposes such as anti-sticking of the powder, corrosion prevention, strength enhancement and improvement in wear resistance, it is possible to subject the screens to plating, painting, abrasion, heat treatment, chemical treatment, etc.

(Embodiment 7)

Figure 14:
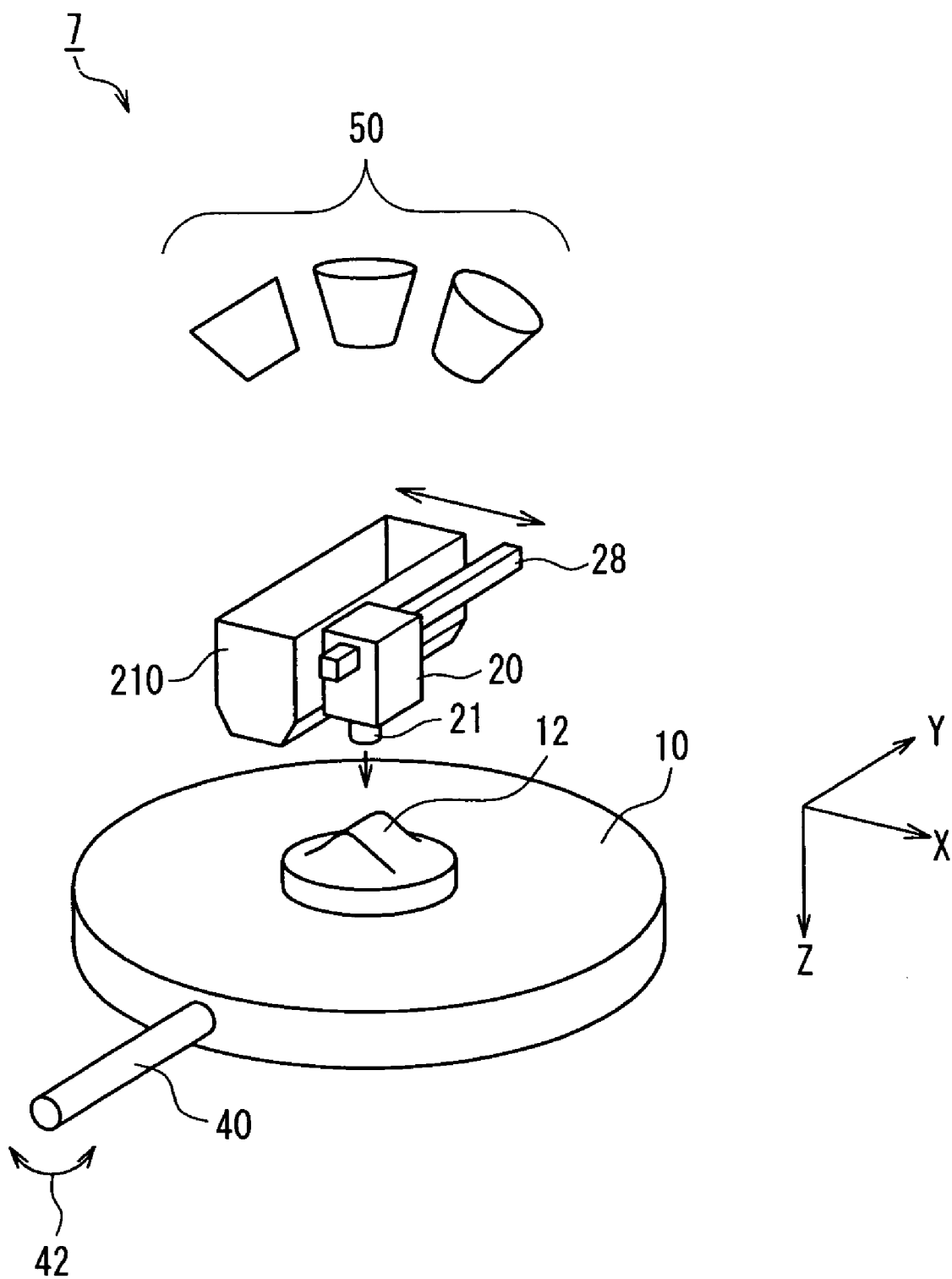
FIG. 14 is a perspective view showing a schematic configuration of a layered-object forming apparatus according to Embodiment 7 of the present invention.

FIG. 14 is a perspective view showing a schematic configuration of a layered-object forming apparatus 7 according to Embodiment 7 of the present invention. Constituent elements that are the same as those in FIG. 1 are assigned the same reference numerals, and the detailed description thereof will be omitted.

The following description mainly is directed to points of Embodiment 7 that are different from Embodiment 6.

The layered-object forming apparatus 7 according to Embodiment 7 has a multilayer screen powder feeder (in the following, simply referred to as a "powder feeder") 210, similarly to the layered-object forming apparatus 6 according to Embodiment 6. However, unlike the powder feeder 200 in Embodiment 6, in the powder feeder 210 according to Embodiment 7, the opening provided in the lower surface of the powder reservoir is rectangular, and the plurality of screens attached to this opening also have a rectangular shape. Except that the opening of the powder reservoir and the plurality of screens have different shapes, the powder feeder 210 of the present embodiment is the same as the powder feeder 200 of Embodiment 6 in terms of its configuration and function. The longitudinal direction of the area in the plurality of screens where a large number of minute holes are formed and the longitudinal direction of the opening of the powder reservoir are parallel with the Y-axis direction, and the longitudinal dimensions thereof are larger than the upper surface of the forming table 10.

The powder feeder 210 is disposed similarly to the powder feeder 30 illustrated in Embodiment 1 and used. In other words, the powder is allowed to fall from above the forming table 10 while the powder feeder 210 is moved in the X-axis direction. However, the powder is started and stopped falling by controlling the driving of the driven screen similarly to Embodiment 6. Since the screen has a rectangular shape, the driven screen makes not the rotational motion as in Embodiment 6 but a reciprocating motion along one direction (for example, the Y-axis direction).

The above-described powder feeder 210 moving in the X-axis direction has an advantage in that, in the case where the powder and the liquid have to be consolidated by applying light or heat from above the forming table 10, the powder feeder 210 easily can be moved out of an irradiation zone of the light or heat.

The powder feeder 210 may be attached to a driving mechanism (not shown) that moves the liquid feeder 20 in the X-axis direction. In this way, the powder feeder 210 and the liquid feeder 20 can share the common driving mechanism in the X-axis direction, making it possible to simplify a drive system and a control system and reduce the number of components.

If the driving mechanism that moves the powder feeder 210 in the X-axis direction and the driving mechanism that moves the liquid feeder 20 in the X-axis direction are provided as different members, it may become necessary to provide them at different positions in the Z-axis direction for avoiding the interference between the powder feeder 210 and the liquid feeder 20. In this case, due to an influence of air current, etc., there is a possibility that it becomes difficult to allow the powder or the liquid falling from the feeder arranged far from the forming table 10 to land at desired positions on the forming table 10. When the powder feeder 210 and the liquid feeder 20 share the common driving mechanism in the X-axis direction, they do not interfere with each other. Therefore, they can be disposed close to the forming table 10, so that the landing position accuracy of the powder and the liquid improves.

Furthermore, as described in Embodiment 4, in the case where the upper surface of the powder on the forming table 10 has to be leveled off to achieve a flat surface, the lower end of the powder feeder 210 may be made to function similarly to the leveling member 95 shown in FIG. 6. Alternatively, the leveling member 95 (see FIG. 6) may be attached to the powder feeder 210. With such integration of the members, it is possible to simplify the drive system and the control system and reduce the number of components.

(Embodiment 8)

Figure 15:
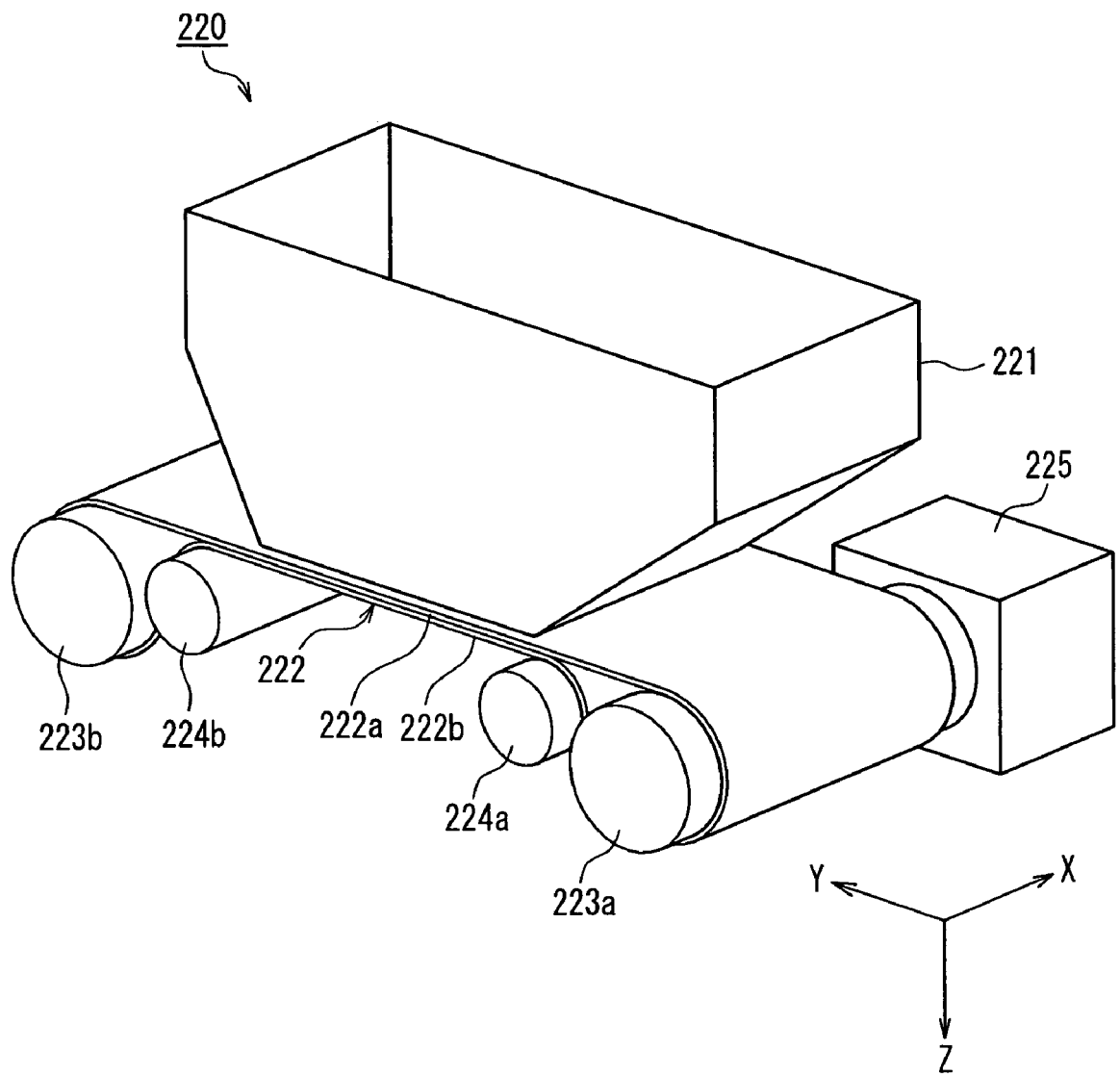
FIG. 15 is a perspective view showing a schematic configuration of a multilayer screen powder feeder according to Embodiment 8 of the present invention.

FIG. 15 is a perspective view showing a schematic configuration of another embodiment of the multilayer screen powder feeder. This multilayer screen powder feeder (in the following, simply referred to as a "powder feeder") 220 includes a powder reservoir 221 and a plurality of (for example, two to six) screens that are provided so as to block the opening (not shown) on the lower surface of the powder reservoir 221. One of the plurality of screens is an endless screen 222 obtained by connecting both ends of a belt-like screen in annular form, and the other screen is a stationary screen that is attached and fixed to the powder reservoir 221 so as to block the opening on the lower surface of the powder reservoir 221. Each of these plurality of screens is provided with a large number of minute through holes (minute holes) through which the powder can pass as described in Embodiment 6.

The endless screen 222 is held at a predetermined position by four rollers 223a, 223b, 224a and 224b, with a predetermined tension being applied thereto. The roller 223a is a live roller to which a driving mechanism 225 is connected, and the rollers 223b, 224a and 224b are follower rollers that can rotate freely. The inside rollers 224a and 224b allow an upper portion 222a and a lower portion 222b of the endless screen 222 to be close to or in contact with each other at the lower surface of the powder reservoir 221.

The driving mechanism 225 causes the endless screen 222 to make a continuous motion in one direction or a reciprocating motion. In this way, the upper portion 222a and the lower portion 222b of the endless screen 222 move in opposite directions.

When the endless screen 222 is stationary, the powder in the powder reservoir 221 does not pass through and fall below the endless screen 222. On the other hand, when the endless screen 222 is driven, the powder passes through the minute holes or the endless screen 222 and falls therebelow. Thereafter, when the driving of the endless screen 222 is stopped, the powder stops falling. As described above, in the present embodiment, the falling of the powder in the powder reservoir 221 on the forming table 10 can be controlled similarly to Embodiment 6. Moreover, such a control can be carried out with a configuration that is simpler and more compact than that in Embodiment 6.

Also, when the endless screen 222 is allowed to make a continuous motion in one direction at a constant speed, the powder falls continuously, and the amount of the powder falling per unit time is constant. On the other hand, when the endless screen 222 is allowed to make a reciprocating motion, the falling of the powder temporarily stops when the motion direction of the endless screen 222 changes and, therefore, becomes intermittent. In other words, the powder feeder 220 in the present embodiment allows the powder to fall continuously and stably, unlike the powder feeder 210 in Embodiment 7.

Figure 16:
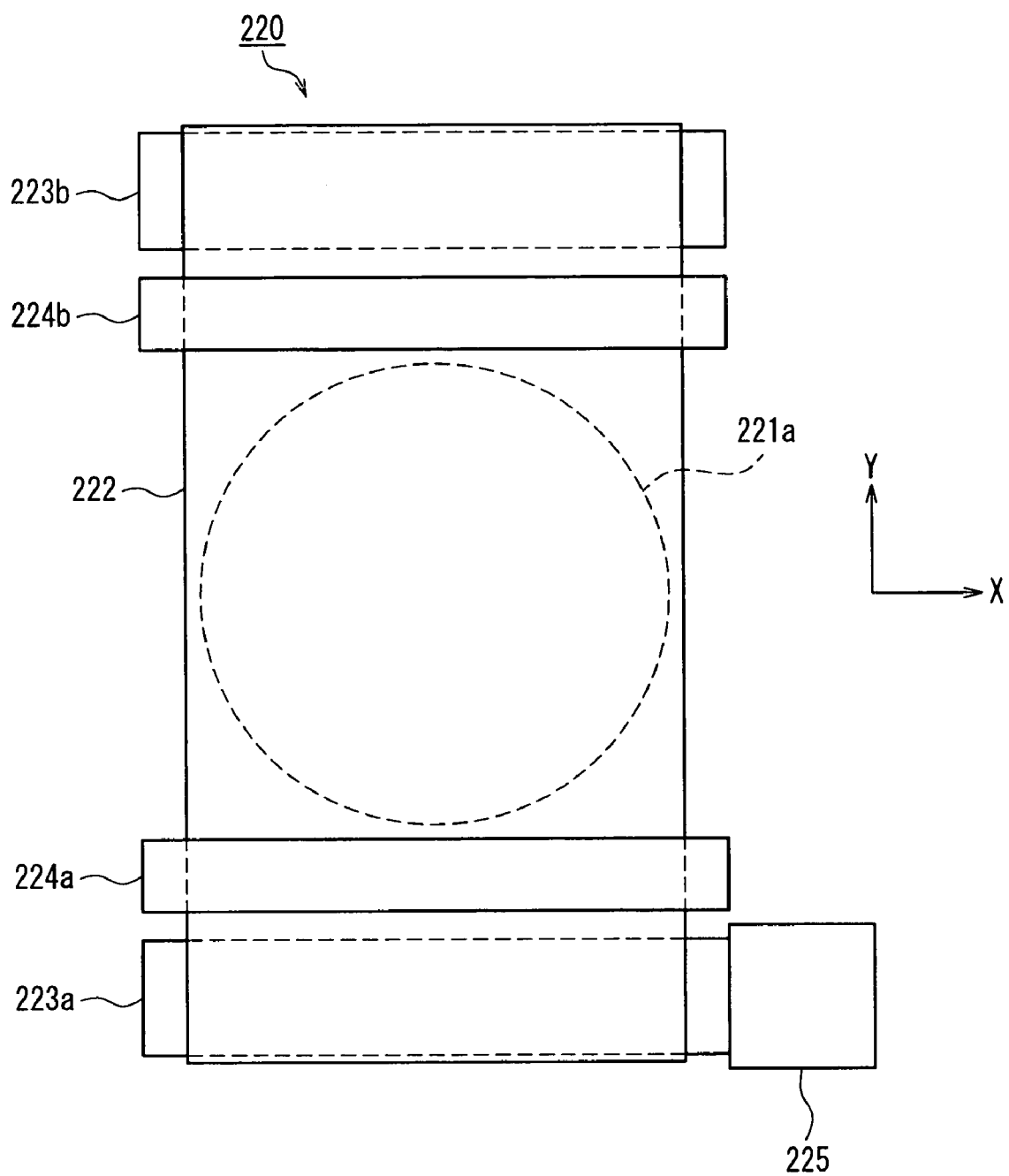
FIG. 16 is a bottom view showing an example of the multilayer screen powder feeder according to Embodiment 8 of the present invention.

FIG. 16 is a bottom view showing an example of the powder feeder 220. Numeral 221a denotes an opening provided in the lower surface of the powder reservoir 221. This opening 221a is circular, and an area in which minute holes of a stationary screen (not shown) to be attached to this opening 221a are formed is also circular. The formation area of the minute holes is equal to or larger than the upper surface of the forming table 10. The powder feeder 220 having the circular opening 221a can disperse the powder on the forming table 10 while the powder feeder 220 is made stationary above the circular forming table 10, for example, similarly to Embodiment 6. When the forming table 10 is circular, by providing the powder reservoir 221 with the circular opening 221a, it is possible to disperse the powder on the forming table 10 without any waste.

Figure 17:
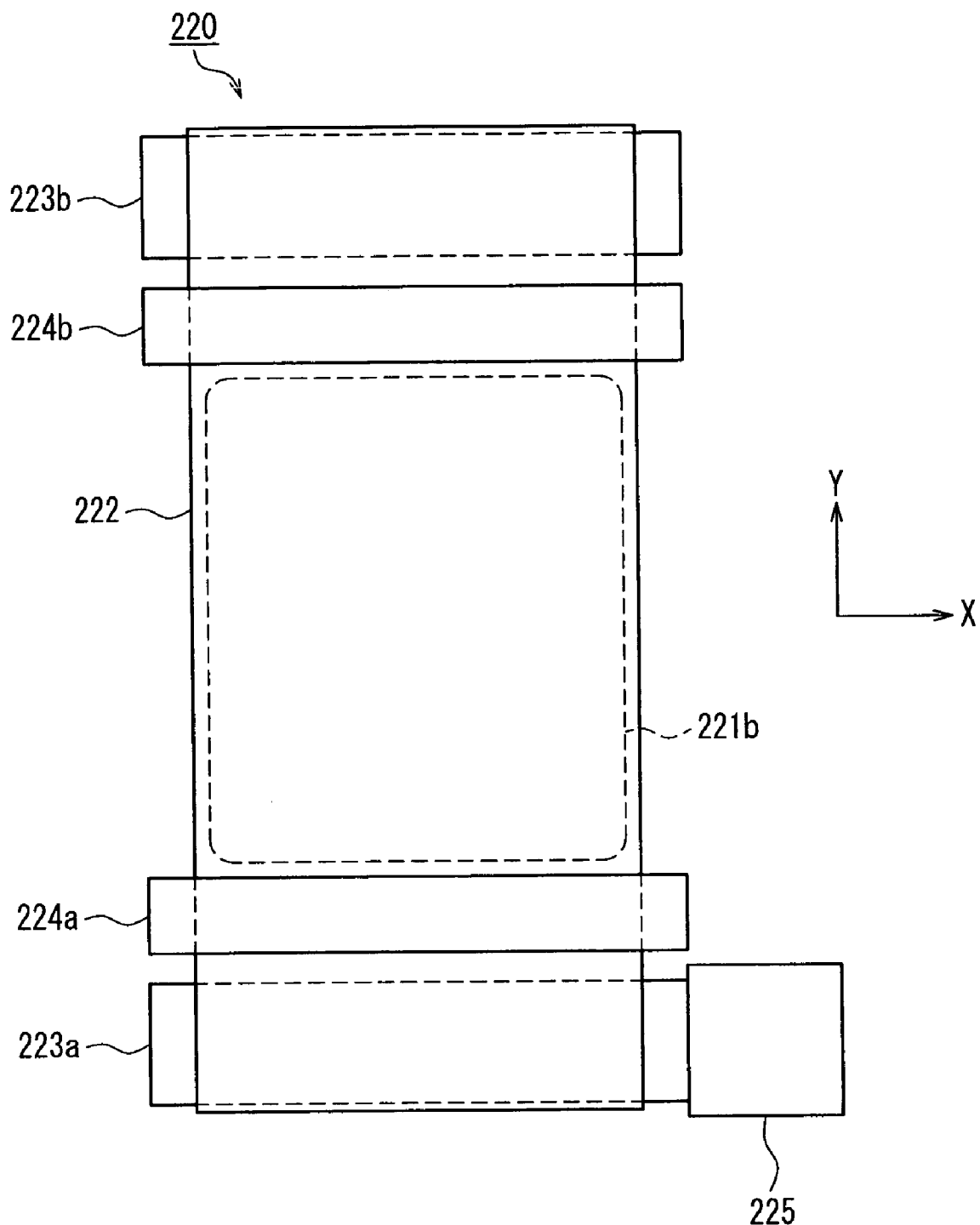
FIG. 17 is a bottom view showing another example of the multilayer screen powder feeder according to Embodiment 8 of the present invention.

FIG. 17 is a bottom view showing another example of the powder feeder 220. Numeral 221b denotes an opening provided in the lower surface of the powder reservoir 221. The opening 221b is rectangular, and an area in which minute holes of a stationary screen (not shown) to be attached to this opening 221b are formed is also rectangular. The longitudinal direction of the formation area of the minute holes is parallel with the Y-axis direction, and the longitudinal dimension thereof is larger than the upper surface of the forming table 10 in the Y-axis direction. The powder feeder 220 having the rectangular opening 221b can disperse the powder on the forming table 10 while the powder feeder 220 is moved in the X-axis direction, for example, similarly to Embodiment 7. Alternatively, when the forming table 10 is rectangular, by providing the powder reservoir 221 with the rectangular opening 221b that is equal to or larger than the forming table 10, it is possible to allow the powder to fall on the forming table 10 without any waste while the powder feeder 220 is kept stationary.

Figure 18:
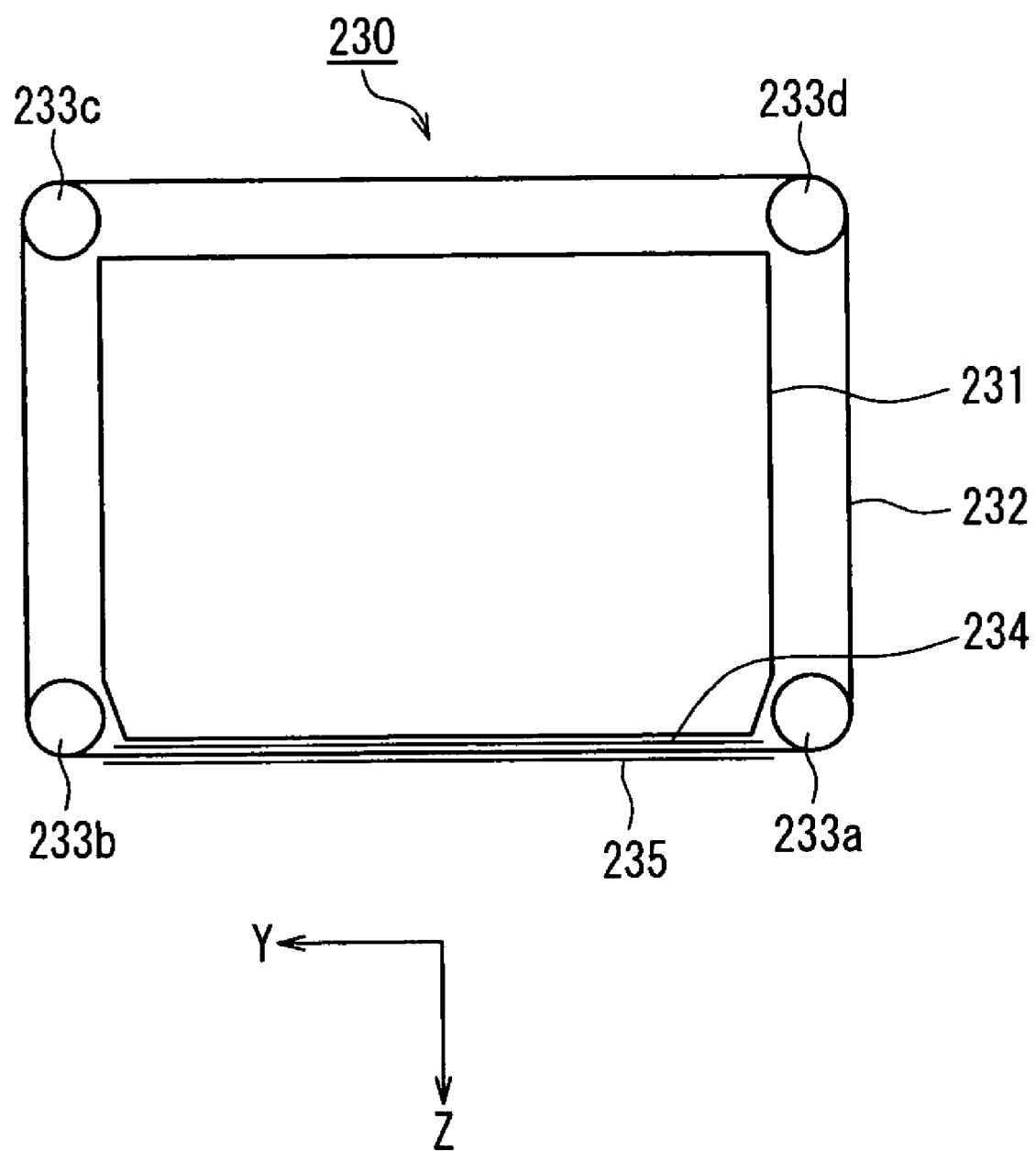
FIG. 18 is a side view showing a schematic configuration of another multilayer screen powder feeder according to Embodiment 8 of the present invention.

FIG. 18 is a side view showing a schematic configuration of another multilayer screen powder feeder (in the following, simply referred to as a "powder feeder") 230. In this powder feeder 230, an endless screen 232 is held by four rollers 233a, 233b, 233c and 233d with a predetermined tension being applied thereto, so as to surround a powder reservoir 231. One of the four rollers 233a, 233b, 233c and 233d is a live roller that is connected to a driving mechanism (not shown), and the rest of them are follower rollers that can rotate freely. In the opening on the lower surface of the powder reservoir 231, stationary screens 234 and 235 are fixed to the powder reservoir 231 so as to sandwich the endless screen 232. In order for the powder to fall, the powder has to pass through the endless screen 222 once in its upper portion 222a and once in its lower portion 222b, namely, twice in total in the powder feeder 220 shown in FIG. 15, whereas the powder only has to pass through the endless screen 232 once in the powder feeder 230 shown in FIG. 18.

Figure 19:
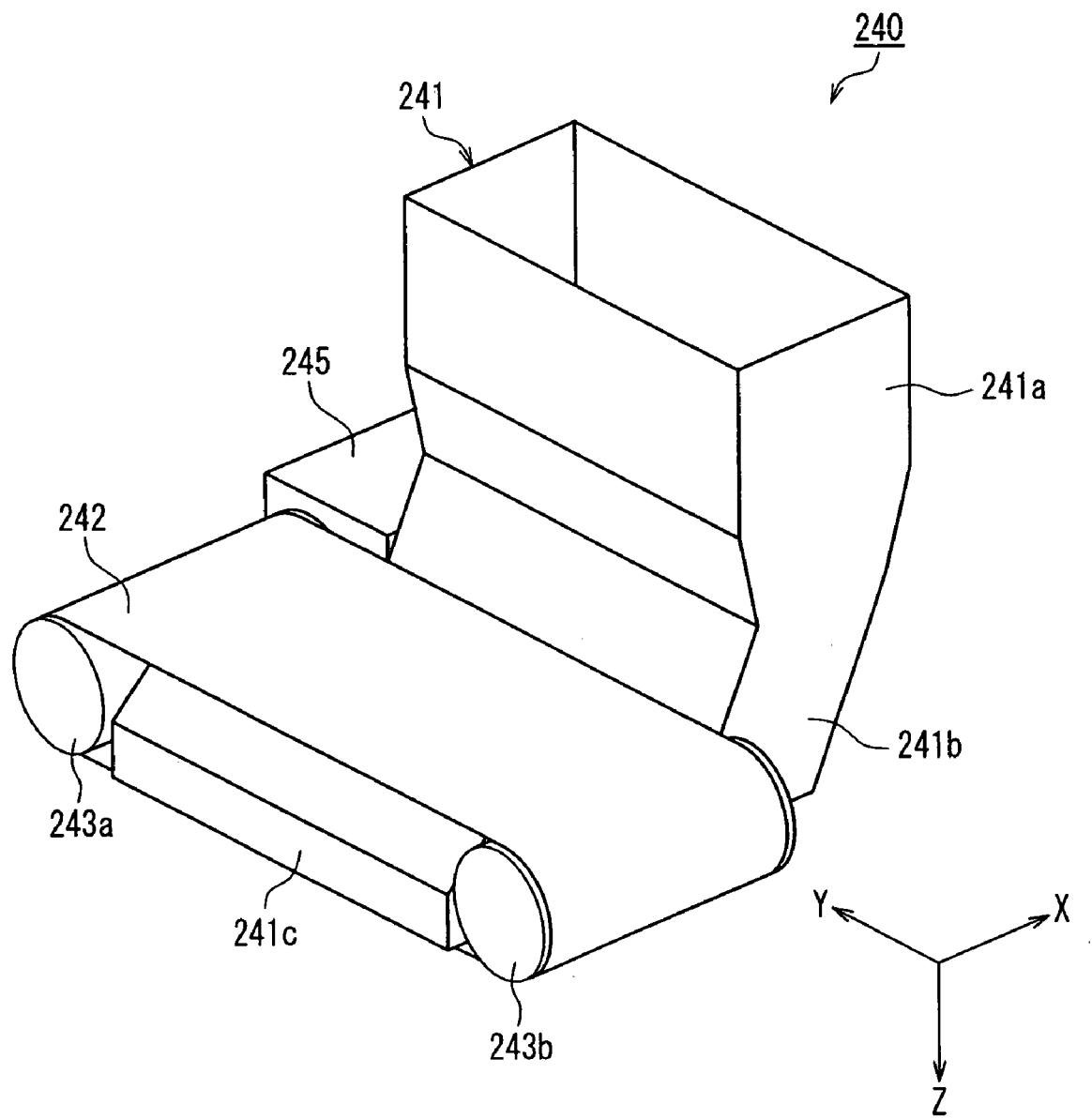
FIG. 19 is a perspective view showing a schematic configuration of yet another multilayer screen powder feeder according to Embodiment 8 of the present invention.

FIG. 19 is a perspective view showing a schematic configuration of yet another multilayer screen powder feeder (in the following, simply referred to as a "powder feeder") 240. In this powder feeder 240, a powder reservoir 241 has a substantially "J" shape when viewed from a direction parallel with the Y axis. The powder reservoir 241 includes an upper powder storing portion 241a, a lower powder applying portion 241c that is parallel with the horizontal plane and a powder supplying passage 241b therebetween. The powder that has been introduced from an opening of the powder storing portion 241a facing upward passes through the powder supplying passage 241b, reaches the powder applying portion 241c, passes through a plurality of screens provided in an opening in a lower surface of the powder applying portion 241c and then falls down. An endless screen 242 is held by two rollers 243a and 243b so as to surround the powder applying portion 241c, with a predetermined tension being applied thereto. The roller 243a is a live roller that is connected to a driving mechanism 245, and the roller 243b is a follower roller that can rotate freely. In the opening in the lower surface of the powder applying portion 24c, a plurality of stationary screens are fixed to the powder applying portion 241c so as to sandwich the endless screen 242 similarly to the powder feeder 230 shown in FIG. 18. In order for the powder to fall, the powder only has to pass through the endless screen 242 once, similarly to the powder feeder 230 shown in FIG. 18. The endless screen 232 has surrounded the entire powder reservoir 231 in the powder feeder 230 shown in FIG. 18, whereas the endless screen 242 surrounds only the powder applying portion 241c, which is part of the powder reservoir 241, in the powder feeder 240 shown in FIG. 19. Accordingly, in the powder feeder 240 shown in FIG. 19, the dimensions of the endless screen 242 and its surrounding area can be reduced. Although the powder storing portion 241a, the powder supplying passage 241b and the powder applying portion 24c are formed as one piece in the powder feeder 240 shown in FIG. 19, it also may be possible to produce the powder storing portion 241a and the powder applying portion 241c independently and then connect them using the powder supplying passage 241b formed of a hard or soft duct or tube or the like.

FIGS. 11 to 19 merely have illustrated examples, and the multilayer screen powder feeder in the present invention is not limited to them. The shape of the multilayer screen powder feeder and the dimension of each part can be modified suitably considering various constraints imposed when mounted on the layered-object forming apparatus, the properties of the powder to be used, the manufacturing process conditions of the three-dimensional structure, etc.

(Embodiment 9)

A layered-object forming apparatus according to Embodiment 9 includes a dividing plate powder feeder (in the following, simply referred to as a "powder feeder") 300 shown in FIG. 20, instead of the powder feeder 30 in the layered-object forming apparatus 1 according to Embodiment 1.

The powder feeder 300 includes a powder reservoir 301 in which the powder is introduced and stored, a dividing portion 310, a guide tube 302 that connects the powder reservoir 301 and the dividing portion 310 and guides the powder from the powder reservoir 301 to the dividing portion 310, and an opening and closing valve 303 that is provided at a lower end of the guide tube 302.

The dividing portion 310 includes a substrate 311 that is inclined at an angle θ (see FIG. 21, which will be described later) with respect to the X axis and has a substantially isosceles triangular shape, and a plurality of dividing plates 312 that are fixed onto the substrate 311 and have a substantially "Λ" shape (a wedge shape). The plurality of dividing plates 312 are arranged divergently, like the arrangement of pins in tenpin bowling. More specifically, the plurality of dividing plates 312 are arranged along a plurality of straight lines that are parallel with a horizontal direction. A row of the dividing plates 312 along one straight line that is parallel with the horizontal direction is referred to as a "tier." The plurality of dividing plates 312 are divided into a plurality of tiers in a vertical direction, and $2^{N-1}$ dividing plates 312 are arranged in the Nth tier (N is a natural number) from the top. A top portion of the substantially "Λ"-shaped dividing plate 312 included in the first tier is located below the opening and closing valve 303, and top portions of the dividing plates 312 included in the N+1th tier are located below both lower ends of the substantially "Λ"-shaped dividing plate 312 included in the Nth tier.

A powder flow that has passed through the powder reservoir 301, the guide tube 302 and the opening and closing valve 303 in this order and flowed into the dividing portion 310 is divided into two by the single dividing plate 312 in the first tier and then divided into four by the two dividing plates 312 in the second tier. Thereafter, the powder flow advances downward while being divided in the Y-axis direction in the similar manner. In this way, the powder flow that has flowed from the opening and closing valve 303 into the dividing portion 310 is divided into $2^N$ powder flows via the dividing plates 312 in the Nth tier. The amount of each powder flow is as $½^N$ times as great as the amount of the powder flow passing through the opening and closing valve 303.

For example, in the case where there are ten tiers of the plurality of dividing plates 312, the powder flow is divided into 1024 flows. When the cross-sectional area of the powder flow passing through the opening and closing valve 303 is 50 mm$^2$, the cross-sectional area of each of the 1024 divided powder flows is about 0.049 mm$^2$, which achieves a fine flow sufficient for dispersing the powder on the forming table 10.

The powder feeder 300 moves in the X-axis direction over the forming table 10 while allowing the powder to fall, similarly to the powder feeder 30 in Embodiment 1.

There arises a time lag from the time when the opening and closing valve 303 is opened (or closed) until the powder starts (or stops) falling from the powder feeder 300. Accordingly, it is necessary to control the opening and closing valve 303 considering this time lag.

Since the powder feeder 300 of the present embodiment in which the plurality of dividing plates 312 are arranged can increase the amount of powder that is allowed to fall per unit time, it has an advantage in that the moving speed of the powder feeder 300 in the X-axis direction can be raised. Consequently, it is possible to shorten the time necessary for dispersing the powder. When the thickness of each of the consolidated portion layers has to be reduced so as to increase the number of the consolidated portion layers, the effects become particularly prominent because it is possible to shorten considerably the time necessary for forming a three-dimensional structure.

Figure 20:
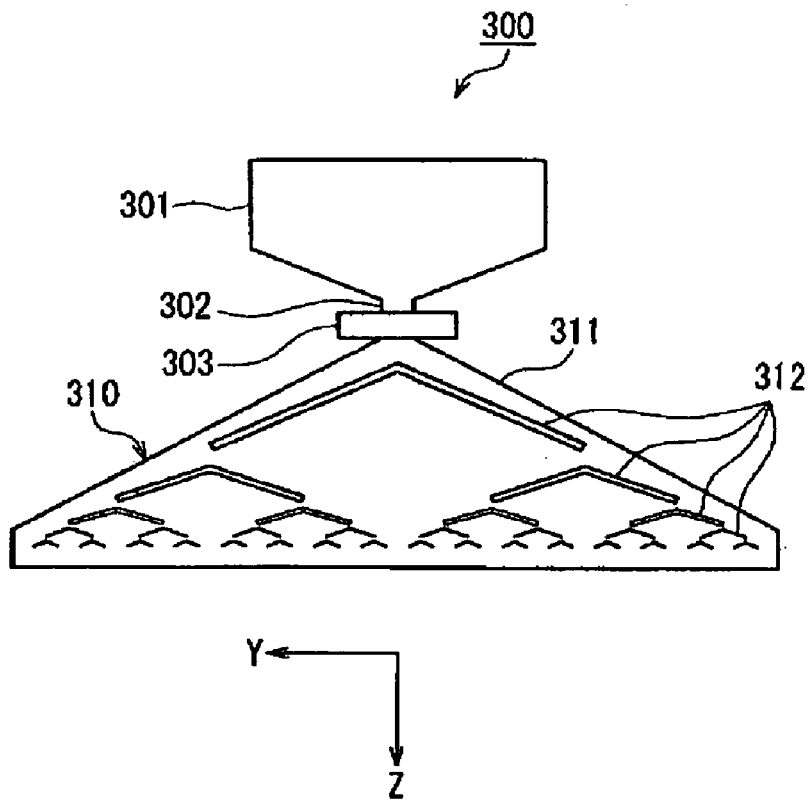
FIG. 20 is a front view showing a schematic configuration of a dividing plate powder feeder according to Embodiment 9 of the present invention.

Although FIG. 20 has illustrated the substantially "Λ"-shaped dividing plates 312, the shape of the dividing plates in the present invention is not limited to this as long as a single powder flow can be divided equally into two powder flows. For example, a plate shape, a rod shape, a triangular shape or a variation thereof may be adopted.

The width (the dimension in the Y-axis direction in FIG. 20) of the dividing plate 312 varies depending on which tier from the top this dividing plate 312 is arranged in. In general, as shown in FIG. 20, the width of the dividing plate 312 decreases from the top to the bottom. When the dividing plates 312 in the lowermost tier are too wide, the space between adjacent powder flows is large, making it difficult to disperse the powder on the forming table 10 uniformly. Conversely, when the dividing plates 312 in the lowermost tier are too narrow, it becomes necessary to increase the number of the dividing plates 312 included in the lowermost tier in order to disperse the powder over a wide range, so that the number of tiers has to be increased, and thus a large number of the dividing plates 312 need to be arranged on the substrate 311. Accordingly, the width of the dividing plates 312 in each tier is determined considering the amount (cross-sectional area) of each powder flow passing between the dividing plates 312 in the lowermost tier and the space between the adjacent powder flows.

When the height (the dimension in the Z-axis direction in FIG. 20) of the dividing plate 312 is too large, the dimension of the substrate 311 in the Z-axis direction is large. Consequently, the practicality of the powder feeder 300 may lower, an increase in the dimension in the Z-axis direction and weight of the dividing portion 310 may impair the mobility of the dividing portion 310 in the X-axis direction, and the interference with other devices such as the liquid feeder 20 may occur. Conversely, when the height of the dividing plate 312 is too small, a gentler inclination of two sides of the dividing plate 312 along which the powder flow flows may deteriorate the fluidity and dividing performance of the powder flow and the strength of the dividing plate 312 may lower. It is appropriate to determine the height of the dividing plate 312 with the foregoing in mind.

The number of the tiers of the plurality of dividing plates 312 arranged on the substrate 311 is determined considering the cross-sectional area of the powder flow passing through the opening and closing valve 303, the number of the powder flows after passing between the dividing plates 312 in the lowermost tier and the cross-sectional area of each of these powder flows. In general, three or more tiers are preferable.

Although FIG. 20 has illustrated the example in which the $2^{N-1}$ dividing plates 312 are arranged in the Nth tier (N is a natural number) from the top, the present invention is not limited to this. For example, in the case where the width (the dimension in the Y-axis direction in FIG. 20) of the powder flow that has passed through the opening and closing valve 303 is large, a plurality of dividing plates 312 may be arranged in the first tier. Also, it is appropriate that more dividing plates 312 be included in the N+1th tier than in the Nth tier. For example, a plurality of dividing plates 312 may be arranged so that the powder flow passing between the adjacent dividing plates 312 in the Nth tier is divided into two by the single dividing plate 312 in the N+1th tier.

Figure 21:
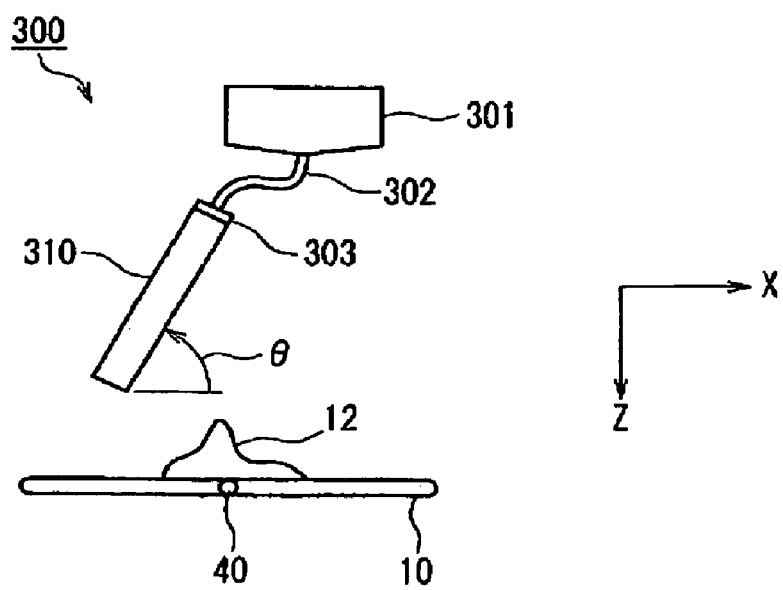
FIG. 21 is a side view showing a schematic configuration of the dividing plate powder feeder according to Embodiment 9 of the present invention.

FIG. 21 is a side view showing the powder feeder 300. At the time of dispersing the powder, the dividing portion 310 of the powder feeder 300 is moved in the X-axis direction by a driving mechanism, which is not shown in the figure, while allowing the powder to fall from above the base 12. In the present example, the powder reservoir 301 is fixed to a position higher than the forming table 10, and the guide tube 302 connecting the powder reservoir 301 and the dividing portion 310 is formed of a material having flexibility and elasticity. This makes it possible to supply the powder from the fixed powder reservoir 301 to the moving dividing portion 310 in a stable manner regardless of the position of the dividing portion 310.

The angle θ that the substrate 311 of the dividing portion 310 forms with the X axis can be set freely within the range from 3° to 90°. The angle θ is varied according to the properties of the powder to be used and the shape and arrangement of the dividing plates 312, thereby adjusting the amount of the powder flow.

(Embodiment 10)

Figure 22:
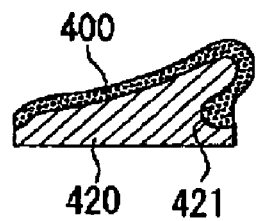
FIG. 22 is a sectional view showing an example of a three-dimensional structure according to Embodiment 10 of the present invention.

FIG. 22 is a sectional view showing an example of a three-dimensional structure 400 formed on a base 420. In order to form such a three-dimensional structure 400, it is necessary to form a consolidated portion also in a recess (an undercut) 421 formed in a peripheral wall of the base 420. Thus, the three-dimensional structure 400 cannot be formed simply by allowing the liquid and the powder to fall from above the base 12 as described in Embodiment 1. Such a three-dimensional structure 400 can be produced by adding to the layered-object forming apparatus in Embodiment 1 an inclination mechanism that can set an inclination angle of an upper surface of the forming table 10 with respect to a horizontal plane freely at the time of dispersing the liquid and powder. For example, a function of the inclination mechanism may be added to the rotation driving mechanism connected to the arm 40 for flipping the forming table 10.

In the following, the method for producing the three-dimensional structure 400 will be described with reference to FIGS. 23A to 23D. For simplification of drawings, FIGS. 23A to 23D only illustrate the forming table 10, the base 420 and a consolidated portion formed on the base 420 and omit other constituent members in a layered-object forming apparatus.

Figure 23A:
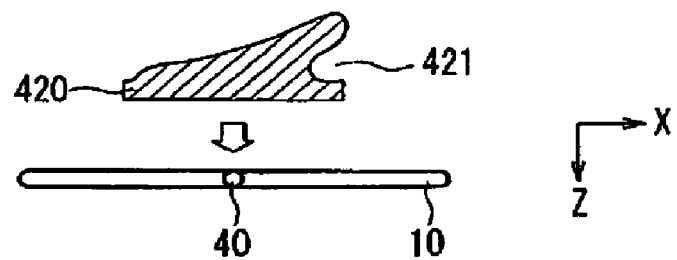
FIG. 23A is a sectional view showing a process in a method for producing the three-dimensional structure according to Embodiment 10 of the present invention.

First, as shown in FIG. 23A, the base 420 is fixed onto the forming table 10 whose upper surface is set to be parallel with the horizontal plane. The peripheral wall of this base 420 is provided with the recess (the undercut) 421, which cannot be seen when the base 420 is viewed from above along the direction parallel with the Z axis.

Figure 23B:
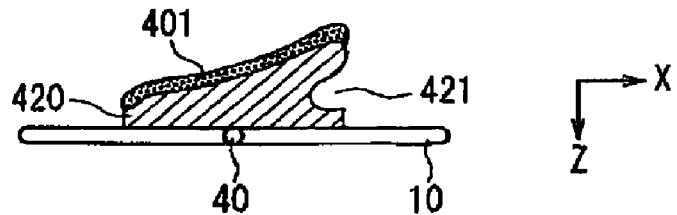
FIG. 23B is a sectional view showing a process in the method for producing the three-dimensional structure according to Embodiment 10 of the present invention.

Next, similarly to the discussions in Embodiments 1 to 3, applying the liquid, allowing the powder to fall and removing the unconsolidated powder are repeated a predetermined number of times, thereby forming a consolidated portion layer 401 with a necessary thickness on a predetermined area on the base 420 that is seen from above when the upper surface of the forming table 10 is set to be parallel with the horizontal plane (see FIG. 23B). Here, the liquid is applied and the powder is allowed to fall, with the upper surface of the forming table 10 being set to be parallel with the horizontal plane. At this time, the consolidated portion layer 401 is not formed in the recess 421 of the base 420.

Figure 23C:
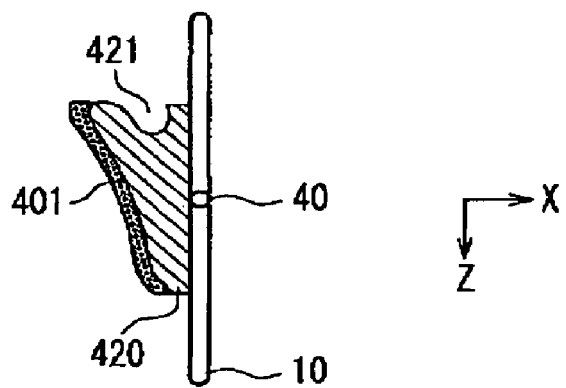
FIG. 23C is a sectional view showing a process in the method for producing the three-dimensional structure according to Embodiment 10 of the present invention.
Figure 23D:
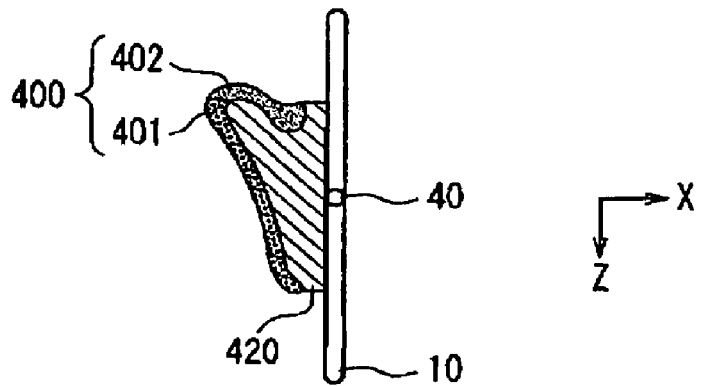
FIG. 23D is a sectional view showing a process in the method for producing the three-dimensional structure according to Embodiment 10 of the present invention.

Subsequently, the base 420 is inclined using the inclination mechanism so that an area where no consolidated portion layer 401 is formed in FIG. 23B, in particular, the recess 421, on the surface of the base 420 faces upward (see FIG. 23C). Similarly to the discussions in Embodiments 1 to 3, applying the liquid, allowing the powder to fall and removing the unconsolidated powder are repeated a predetermined number of times, thereby forming a consolidated portion layer 402 with a necessary thickness on an area including the recess 421 on the surface of the base 420 (see FIG. 23D). Here, the liquid is applied and the powder is allowed to fall, with the forming table 10 being inclined as shown in FIG. 23C. In this manner, the three-dimensional structure 400 shown in FIG. 22 can be formed on the base 420.

As described above, in accordance with Embodiment 10, even in the case where an entire area on the base in which the consolidated portion layer needs to be formed cannot be seen at one time from any single direction, the consolidated portion is formed while varying the orientation (attitude) of the base, thus making it possible to form a desired three-dimensional structure on the base.

In order to form a three-dimensional structure according to the present embodiment, it is appropriate to resolve three-dimensional shape data of a three-dimensional structure to be formed into plural data according to the number of variations in the base orientation and compute liquid delivery control data, etc. for each orientation.

Although the above description has been directed to the case in which the base 420 has the recess 421, the present embodiment also can be applied to the case of forming a three-dimensional structure on a base without the recess 421.

In the above description, after the consolidated portion layer 401 that is formed by consolidation of the liquid and the powder and has a desired thickness is formed on the base 420 by repeating applying the liquid to and allowing the powder to fall on the base 420 facing a first direction as shown in FIG. 23B, the consolidated portion layer 402 that is formed by consolidation of the liquid and the powder and has a desired thickness is formed on the base 420 by repeating applying the liquid to and allowing the powder to fall on the base 420 facing a second direction as shown in FIG. 23C. In other words, the surface of the base 420 on which the three-dimensional structure 400 is to be formed is divided into a first area and a second area, a portion 401 in the first area in the three-dimensional structure 400 is completed, and then a portion 402 in the second area in the three-dimensional structure 400 is completed.

However, the present invention is not limited to this. For example, the three-dimensional structure 400 also may be formed on the base 420 by alternating and repeating a process in which the liquid is applied to and the powder is allowed to fall on the base 420 facing the first direction as shown in FIG. 23B so as to form a single consolidated portion layer formed by consolidation of the liquid and the powder on the base 420 and a process in which the liquid is applied to and the powder is allowed to fall on the base 420 facing the second direction as shown in FIG. 23C so as to form a single consolidated portion layer formed by consolidation of the liquid and the powder on the base 420. In other words, a single consolidated portion layer may be formed alternately in the first area and the second area.

Although the three-dimensional structure has been formed while using two base orientations in the above-described embodiment, the number of variations in the base orientation is not limited to two in the present invention but can be changed suitably according to the surface shape (for example, the number or degree of the recesses) of the base. It should be noted however that a larger number of variations in the base orientation sometimes may cause unevenness at the borders between the consolidated portion layers formed at the individual orientations, resulting in deteriorated shape accuracy of the three-dimensional structure, or increase the time for forming a three-dimensional structure considerably. Therefore, it is not preferable to vary the base orientations more than necessary. In practice, the number of variations in the base orientation preferably is 2 to 10 and further preferably is 2 to 6.

(Embodiment 11)

Figure 24:
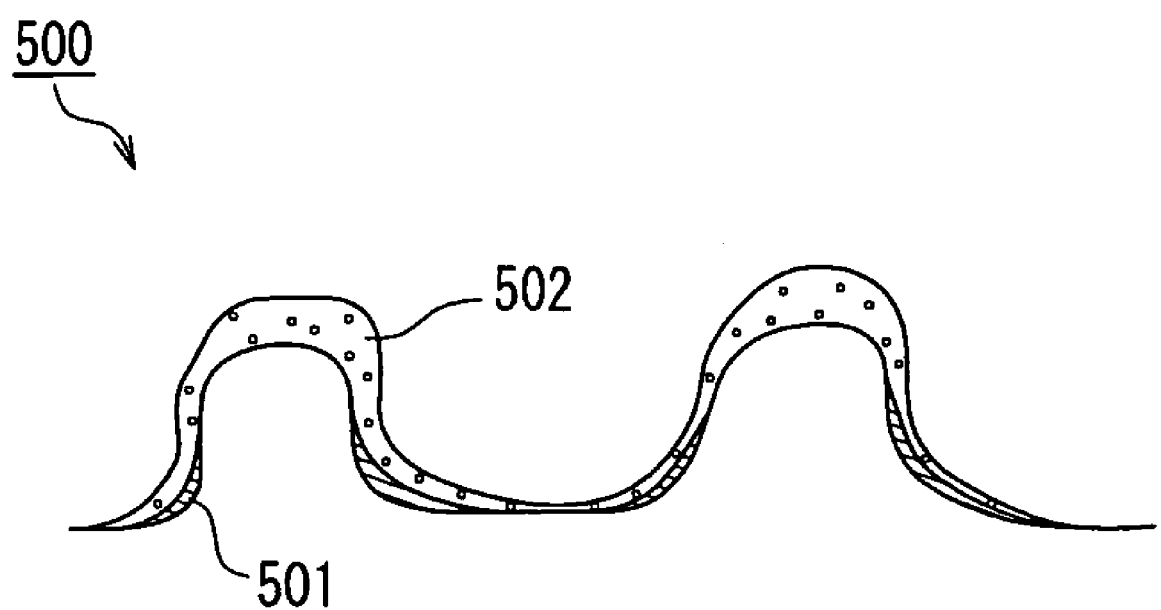
FIG. 24 is an end view showing an example of a three-dimensional structure according to Embodiment 11 of the present invention.

FIG. 24 is a lateral end view showing an example of a three-dimensional structure 500 according to Embodiment 11 of the present invention. This three-dimensional structure 500 is a prosthetic appliance such as a partial denture including a metallic portion 501 and a resin portion 502.

The following is a description of the method for producing the three-dimensional structure 500 using the layered-object forming apparatus according to the present invention.

Figure 25A:
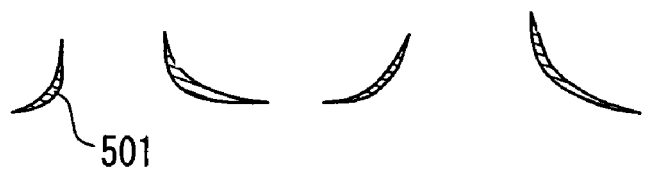
FIG. 25A is an end view showing a process in a method for producing the three-dimensional structure according to Embodiment 11 of the present invention.

First, as shown in FIG. 25A, the metallic portion 501 is formed. The method for forming the metallic portion 501 is not limited particularly but can be a conventionally known method. For example, it is possible to use a method of manual work, a method of cutting a metallic material based on three-dimensional shape data of the metallic portion 501 using CAD/CAM, a method of layering metallic powder and melting and sintering the metallic powder by irradiating a laser beam or the like based on three-dimensional shape data of the metallic portion 501 using CAD/CAM, or the like. The metallic portion 501 may be subjected to a surface treatment, for example, polishing to give a shine to a surface that contacts a mucosal surface in a patient's mouth or smoothing the border with the resin portion 502 by sandblasting, as necessary.

Figure 25B:
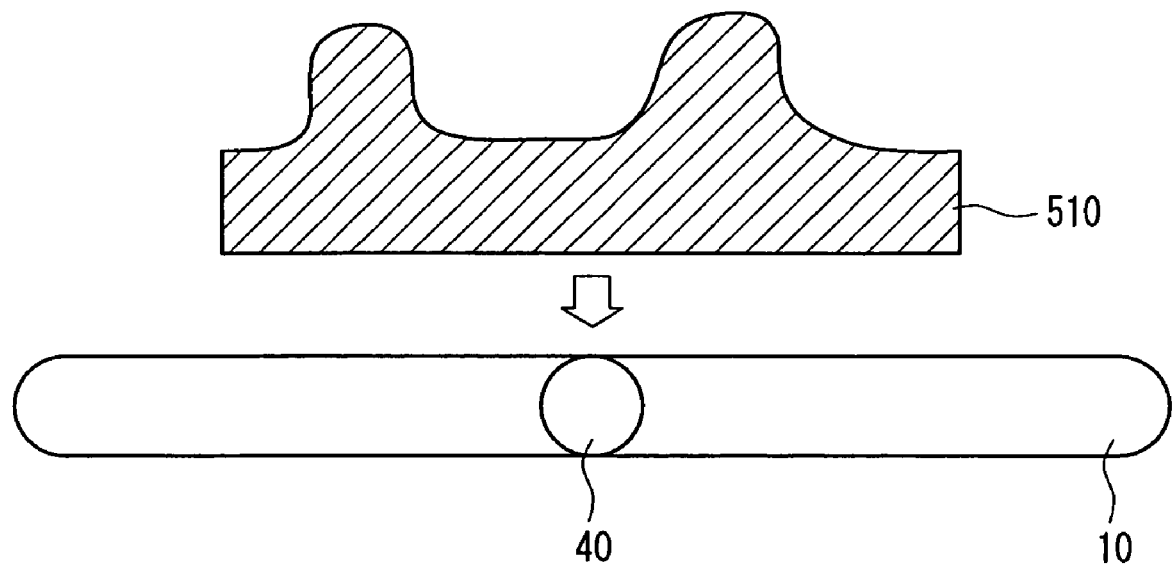
FIG. 25B is a sectional view showing a process in the method for producing the three-dimensional structure according to Embodiment 11 of the present invention.

In a process different from the above, as shown in FIG. 25B, a base 510 is fixed onto the forming table 10 of the layered-object forming apparatus. The base 510 is a replica of a patient's alveolar ridge. The upper surface of the base 510 has the same shape as the mucosal surface in the patient's mouth.

Figure 25C:
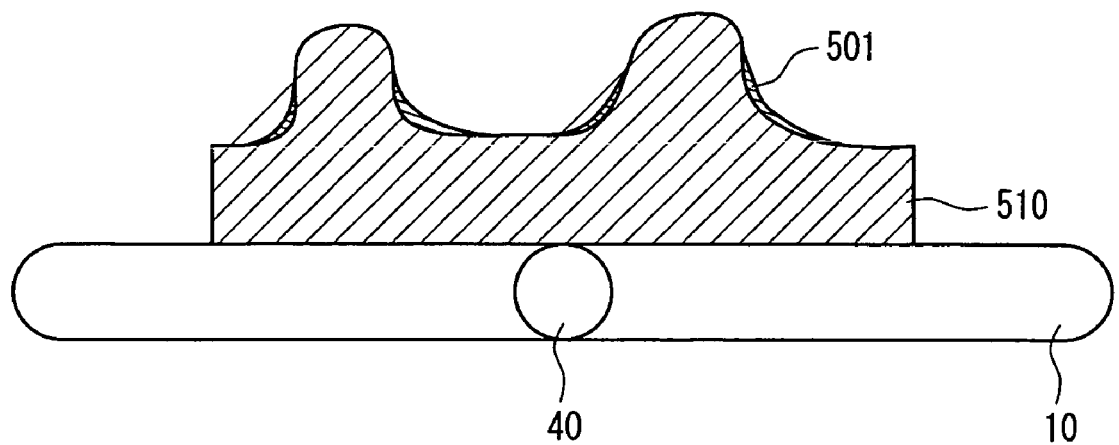
FIG. 25C is a sectional view showing a process in the method for producing the three-dimensional structure according to Embodiment 11 of the present invention.

Next, as shown in FIG. 25C, the metallic portion 501 obtained in FIG. 25A is disposed on the base 510.

Figure 25D:
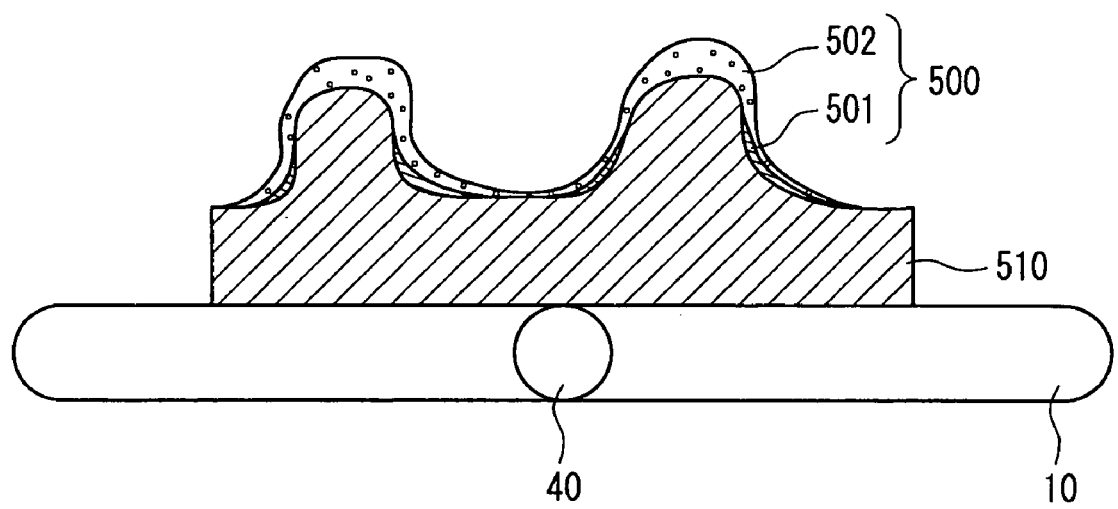
FIG. 25D is a sectional view showing a process in the method for producing the three-dimensional structure according to Embodiment 11 of the present invention.
Figure 26:
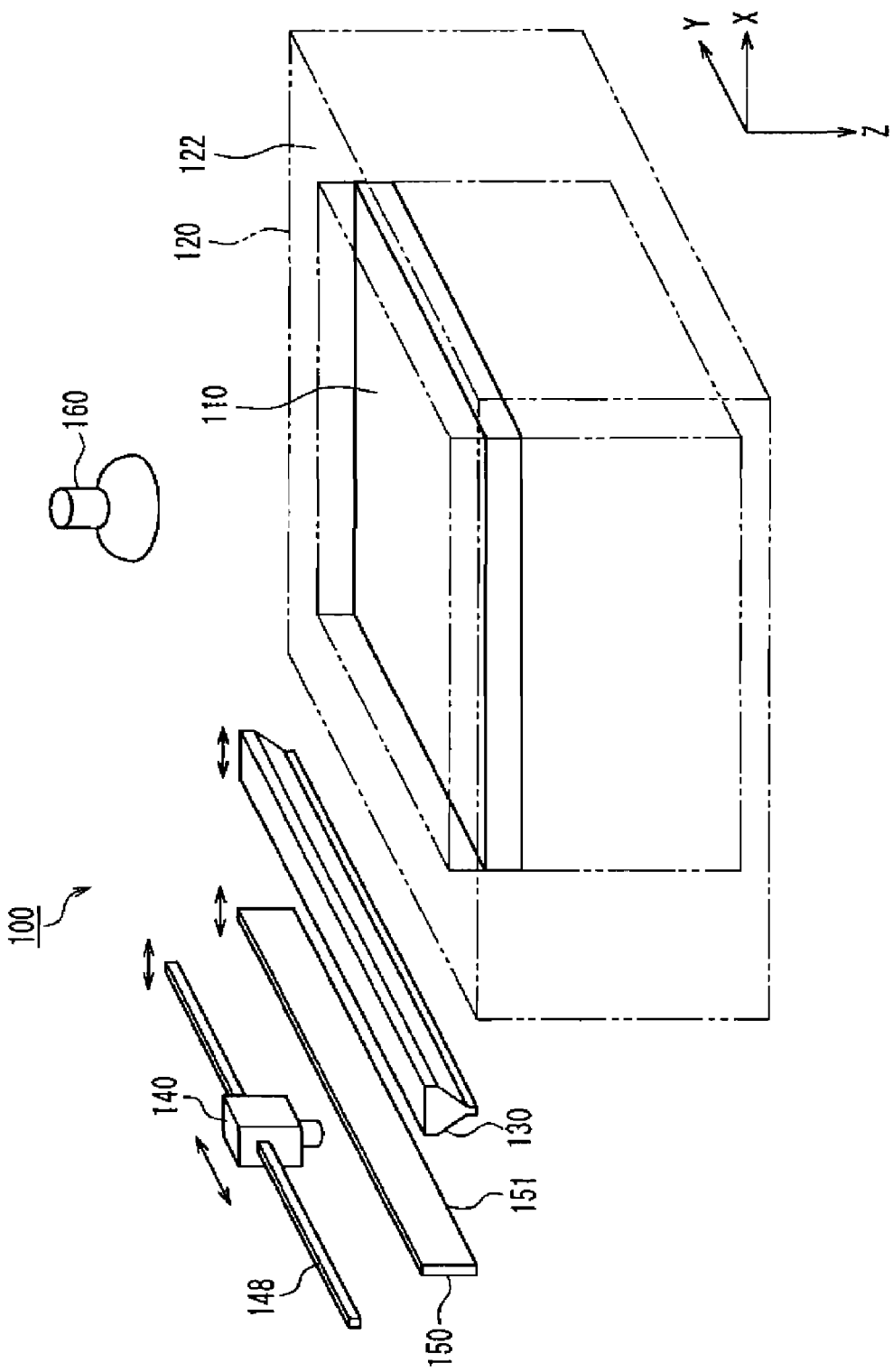
FIG. 26 is a perspective view showing a schematic configuration of an example of a conventional layered-object forming apparatus.
Figure 27A:
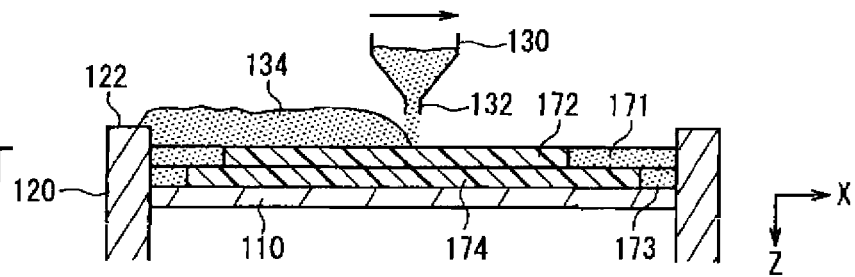
FIG. 27A is a sectional view showing a process in a method for producing a three-dimensional structure using the conventional layered-object forming apparatus.
Figure 27B:
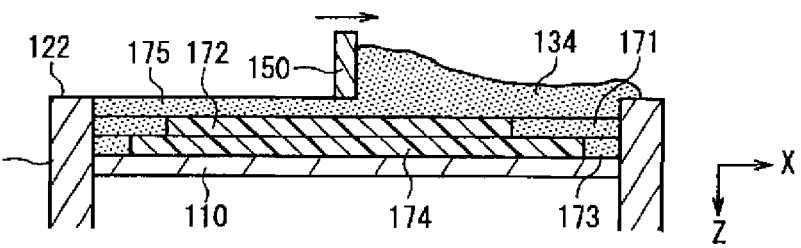
FIG. 27B is a sectional view showing a process in the method for producing a three-dimensional structure using the conventional layered-object forming apparatus.
Figure 27C:
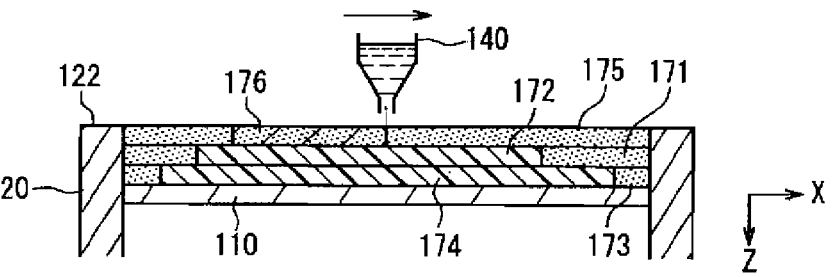
FIG. 27C is a sectional view showing a process in the method for producing a three-dimensional structure using the conventional layered-object forming apparatus.
Figure 27D:
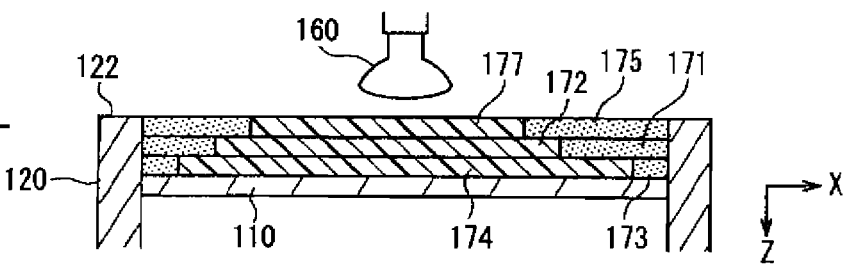
FIG. 27D is a sectional view showing a process in the method for producing a three-dimensional structure using the conventional layered-object forming apparatus.
Figure 27E:
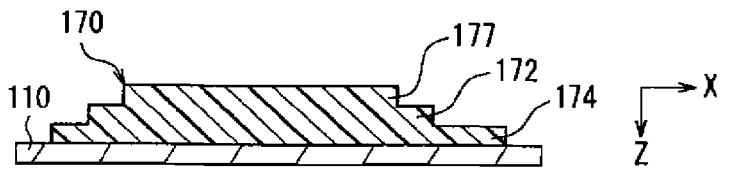
FIG. 27E is a sectional view showing a process in the method for producing a three-dimensional structure using the conventional layered-object forming apparatus.

Thereafter, using the forming apparatus according to the present invention, by repeating applying the liquid, allowing the powder to fall and removing the unconsolidated powder a predetermined number of times, a consolidated portion layer to be the resin portion 502 is formed, thus achieving the three-dimensional structure 500 (see FIG. 25D).

Then, the three-dimensional structure 500 is removed from the base 510 and subjected to after treatments such as modification of details and surface polishing as necessary, thus completing a dental prosthetic appliance.

EXAMPLE 1

Using the layered-object forming apparatus 1 described in Embodiment 1, a complete base for a full denture of an upper jaw was produced.

[Preparation of Powder]

As the powder, a mixture of 100 parts by weight of spherical particles (with an average grain size of 70 μm) of copolymer of methyl methacrylate and ethyl methacrylate at weight ratio of 1:1 and 1 part by weight of benzoyl peroxide was used.

[Preparation of Liquid]

As the liquid, a composition obtained by blending 10 parts by weight of ethylene glycol dimethacrylate monomer and 3 parts by weight of diethanol para-toluidine into 90 parts by weight of methyl methacrylate monomer that was colored by an edible ink was used. Based on this liquid, liquid 1 adjusted to be the color of gum and liquid 2 adjusted to be transparent were prepared.

[Generation of Liquid Delivery Control Data]

In order to achieve a desired color tone, color tone data were added to three-dimensional shape data of a complete base having holes in which artificial teeth were to be fitted, thus generating liquid delivery control data. More specifically, application position data for the liquids 1 and 2 were generated so that a surface layer to a depth of about 1 mm from an external surface was formed of the liquid 2 and part inside this surface layer was formed of the liquid 1.

[Specification of Layered-Object Forming Apparatus]

A base 12, which was a replica of a patient's alveolar ridge, was fixed onto a 100 mm×100 mm square forming table 10.

A powder feeder 30 included a slit 32 having a width of 100 mm in the Y-axis direction and a width of 3 mm in the X-axis direction (moving direction).

A liquid feeder 20 included two nozzles 21 that ejected the liquids 1 and 2, respectively, when driven by a piezoelectric element. More specifically, 318SLX manufactured by Konica Minolta Technology Center, Inc., which was an ink jet head driven by a piezoelectric element, was used as the nozzles 21. As a device for controlling this ink jet head, an ink jet head evaluation kit KIE2 manufactured by Konica Minolta Technology Center, Inc. was used. As a control program, software included in this control device was used. A liquid reservoir tank with a capacity of 300 cc was connected to each of the two nozzles 21 via a tube.

A computer was used to control the movement of the powder feeder 30 and the liquid feeder 20, the opening and closing of the slit 32 of the powder feeder 30 and the liquid ejection from the two nozzles 21 of the liquid feeder 20.

[Formation of Three-Dimensional Structure]

Using the layered-object forming apparatus 1 illustrated in FIG. 1, the processes shown in FIGS. 2A to 3D were carried out while controlling the application positions of the liquids 1 and 2 based on the liquid delivery control data described above, thereby producing a complete base on the base 12 that reproduced truly the shape of a mucosal surface in a patient's mouth. Chemical polymerization was employed for polymerizing the liquid.

[After Treatment]

The resultant complete base was removed from the base 12. The surface that had been in contact with the base 12 (an adhesion surface) was formed as a smooth surface along the surface of the base 12 and did not have any steps due to layering. On the other hand, surfaces other than the surface that had been in contact with the base 12 slightly had steps due to layering. These steps due to layering were removed using an ultrasonic mini-cutter MC-20 manufactured by DAIEI DENTAL PRODUCT CO., LTD. Thereafter, the entire surface of the complete base was finished by buffing.

In upper holes in the resultant complete base, artificial teeth of one set of each of front teeth and molar teeth made of hard resin teeth "Veracia" manufactured by SHOFU INC. were made to adhere and fixed using a mixture of powder material of ADFA manufactured by SHOFU INC. and the liquid as an adhesive.

The adhesion surface of the thus obtained complete denture had an extremely high adaptability to the mucosal surface in a patient's mouth.

The time required for producing the complete base was 3 hours and 30 minutes in total, including 30 minutes of designing, 2 hours and 30 minutes of forming and 30 minutes of removing steps and polishing of the surface. This was considerably shorter than the time of about 13 hours required by a conventional general method including mold making, production of replicated model, waxing-up, investing, dewaxing, mold, kneading, polishing, etc.

The invention may be embodied in other specific forms without departing from the spirit or essential characteristics thereof. The embodiments and example disclosed in this application are to be considered in all respects as illustrative and not restrictive, the scope of the invention being indicated by the appended claims rather than by the foregoing description, all changes that come within the meaning and range of equivalency of the claims are intended to be embraced therein.

Industrial Applicability

The present invention is applicable to any fields without any particular limitation and can be utilized for producing various three-dimensional structures. In particular, the present invention can be utilized preferably for manufacturing dental structural materials. For example, the present invention can be utilized for producing dentures used in the field of dental prosthetics, disposable dentures that are worn by persons in need of nursing care or the like who are not able to wash their dentures by themselves and, when become dirty, replaced with new dentures having an identical shape, thereby keeping their mouths clean, mouthpieces that are worn in mouths for protecting teeth against impacts at the time of playing sports, protection appliances for preventing the tooth abrasion or breakage due to teeth grinding, splints used for the purpose of preventing or relieving the disorder due to an anomaly of a temporomandibular joint or treating the anomaly of a temporomandibular joint, appliances for relieving and solving swallowing difficulty, and sensor holders, sensor embedded bodies, paraocclusal splints, etc. used for the purpose of measuring the process of the contact or separation of teeth at the time of jaw motion or mouth opening/closing in dentistry.

The invention claimed is:

1. A layered-object forming apparatus comprising:
a holding mechanism;
a base positioned on the holding mechanism and having an upper surface to be transferred to a lower surface of a three-dimensional structure to be formed on the apparatus, a shape of a mucosal surface in a mouth being reproduced on the upper surface of the base;
a liquid applying device that applies a liquid comprising a polymerizable component to a predetermined position from above the base;
a powder applying device that allows a powder to fall from above the base;
a powder removing device that removes an unconsolidated powder on the base; and
a controller that is configured to control the apparatus to perform a process that comprises (a) a step of applying the liquid with the liquid applying device, (b) a step of applying the powder with the powder applying device, (c) a step of consolidating the applied liquid and the applied powder by polymerizing the liquid, and then (d) a step of removing the powder that has not been consolidated with the liquid with the powder removing device, the process being repeated to form the three dimensional structure on the base,
wherein the controller is configured to control the apparatus so that the liquid is applied first to the base.

2. The layered-object forming apparatus according to claim 1, wherein the holding mechanism is a table on which the base is placed.

3. The layered-object forming apparatus according to claim 1, wherein the holding mechanism is a rod-like member that is inserted in the base.

4. The layered-object forming apparatus according to claim 1, wherein the powder removing device comprises a rotating mechanism for rotating the base and allows the unconsolidated powder to fall by gravity and be removed.

5. The layered-object forming apparatus according to claim 1, wherein the powder removing device comprises an air nozzle for ejecting a gas that blows off and removes the unconsolidated powder by the gas.

6. The layered-object forming apparatus according to claim 1, wherein the powder removing device comprises a suction nozzle for sucking an atmosphere and allows the unconsolidated powder to be sucked into the suction nozzle and removed.

7. The layered-object forming apparatus according to claim 1, further comprising a vibration generating device that vibrates the holding mechanism.

8. The layered-object forming apparatus according to claim 2, further comprising a container surrounding a horizontal periphery of the table, a leveling member that levels off the powder heaped in the container, and a lifting and lowering mechanism that varies a relative position between the container and the table along a height direction.

9. The layered-object forming apparatus according to claim 1, wherein the holding mechanism is a table on which the base is placed,
the layered-object forming apparatus further comprises a container surrounding a horizontal periphery of the table, a leveling member that levels off the powder heaped in the container, and a lifting and lowering mechanism that varies a relative position between the container and the table along a height direction, and
the controller is configured to control the apparatus to perform the repeated process comprising steps (a)-(d), wherein steps of applying the powder into the container by the powder applying device, subsequently leveling off the powder by the leveling member, subsequently applying the liquid by the liquid applying device and then lowering the table relative to the container by the lifting and lowering mechanism are repeated, thereby forming a further three-dimensional structure on the three-dimensional structure.

10. The layered-object forming apparatus according to claim 1, further comprising a three-dimensional measuring device that measures the base or the three-dimensional structure formed on the base.

11. The layered-object forming apparatus according to claim 1, wherein a lower surface of the powder applying device is provided with a plurality of screens that are stacked so as to block an opening formed on the lower surface, each of the plurality of screens is provided with a plurality of holes through which the powder can pass, and falling of the powder is controlled by controlling a movement of at least one of the plurality of screens relative to the other.

12. The layered-object forming apparatus according to claim 11, wherein one of the plurality of screens is an endless screen obtained by connecting both ends of a belt-like screen in annular form.

13. The layered-object forming apparatus according to claim 1, wherein the powder applying device comprises an inclined substrate and a plurality of dividing plates that are arranged on the substrate, the plurality of dividing plates are divided into a plurality of tiers in a vertical direction, more dividing plates are included in an N+1th tier than in an Nth tier from a top when N is a natural number, and each of the dividing plates divides a powder flow from above into two.

14. The layered-object forming apparatus according to claim 1, further comprising an inclination mechanism that varies an orientation of the base to at least two directions including a first direction and a second direction different from the first direction, wherein the apparatus applies the liquid and allows the powder to fall in each of a state where the base faces the first direction and a state where the base faces the second direction.

15. The layered-object forming apparatus according to claim 14, wherein the liquid is applied to and the powder is allowed to fall on the base facing the first direction repeatedly so as to form on the base a first consolidated portion layer that is formed by consolidation of the liquid and the powder, and then the liquid is applied to and the powder is allowed to fall on the base facing the second direction repeatedly so as to form on the base a second consolidated portion layer that is formed by consolidation of the liquid and the powder.

16. The layered-object forming apparatus according to claim 14, wherein the controller controls the apparatus so that a process of applying the liquid to and allowing the powder to fall on the base facing the first direction so as to form on the base a first consolidated portion layer that is formed by consolidation of the liquid and the powder, and a process of applying the liquid to and allowing the powder to fall on the base facing the second direction so as to form on the base a second consolidated portion layer that is formed by consolidation of the liquid and the powder are repeated alternately.

17. The layered-object forming apparatus according to claim 1, wherein the controller controls the apparatus to perform the repeated process, wherein the repeated process consists of applying the liquid with the liquid applying device, applying the powder with the powder applying device, consolidating the applied liquid and applied powder by polymerizing the liquid, and then removing the powder that has not been consolidated with the liquid with the powder removing device.

* * * * *